United States Patent
Carignan et al.

(10) Patent No.: US 9,351,857 B2
(45) Date of Patent: May 31, 2016

(54) METHOD AND APPARATUS FOR JOINT MOTION SIMULATION

(75) Inventors: Forest J. Carignan, Bedford, MA (US); Bruce F. White, Boston, MA (US)

(73) Assignee: Advanced Mechanical Technology, Inc., Watertown, MA (US)

(*) Notice: Subject to any disclaimer, the term of this patent is extended or adjusted under 35 U.S.C. 154(b) by 1202 days.

(21) Appl. No.: 13/295,610

(22) Filed: Nov. 14, 2011

(65) Prior Publication Data
US 2012/0123592 A1    May 17, 2012

Related U.S. Application Data

(60) Provisional application No. 61/413,873, filed on Nov. 15, 2010.

(51) Int. Cl.
*A61F 2/76* (2006.01)
*B25J 17/02* (2006.01)
(Continued)

(52) U.S. Cl.
CPC . *A61F 2/76* (2013.01); *A61F 2/468* (2013.01); *A61F 2/68* (2013.01); *B25J 17/0266* (2013.01);
(Continued)

(58) Field of Classification Search
CPC .............. A61F 2/68; A61F 2002/701; A61F 2002/704; A61F 2002/707; A61F 2002/741; A61F 2002/744; G09B 23/32; B25J 17/0266; Y10T 74/20207; Y10T 74/20348
USPC .......... 700/275; 623/24, 26, 27, 57; 73/865.3, 73/865.4, 866.4
See application file for complete search history.

(56) References Cited

U.S. PATENT DOCUMENTS

| 5,014,719 A | 5/1991 | McLeod |
| 5,127,420 A | 7/1992 | Horvath |

(Continued)

FOREIGN PATENT DOCUMENTS

| JP | 2007-272116 | 10/2007 |
| WO | WO 2009/127171 A1 | 10/2009 |
| WO | WO 2012/068015 A2 | 5/2012 |

OTHER PUBLICATIONS

Fan et al., "A Haptic Feedback System for Lower-Limb Prostheses", IEEE Transactions on Neural Systems and Rehabilitation Engineering, 2008, vol. 16, Issue: 3, pp. 270-277.*

(Continued)

*Primary Examiner* — Crystal J Barnes-Bullock
(74) *Attorney, Agent, or Firm* — Hamilton, Brook, Smith & Reynolds, P.C.

(57) ABSTRACT

A joint motion simulator to simulate biomechanical motion includes a mount to which a prosthetic device is mounted, actuators coupled to the mount to drive the mount, and a programmable controller to drive the actuators to translate the mount and to rotate the mount with a center of rotation controllable independent of translation. The simulator can include a linear actuator to translate the mount in a linear direction substantially parallel to the axis of rotation. The linear actuator can include a piston within a sleeve, the piston being coupled to the mount and being hydraulically driven to translate the mount, and the actuators can be coupled to the sleeve. The controller may be programmed to vary the center of rotation with linear translation and rotation of the mount. Sensors may be included that measure displacement of the actuators. The controller may drive the actuators based on the measured displacement.

38 Claims, 19 Drawing Sheets

(51) Int. Cl.
  A61F 2/68    (2006.01)
  A61F 2/46    (2006.01)
  G09B 23/32   (2006.01)
  A61F 2/70    (2006.01)
  A61F 2/74    (2006.01)
  A61F 2/38    (2006.01)

(52) U.S. Cl.
  CPC . *G09B 23/32* (2013.01); *A61F 2/38* (2013.01); *A61F 2002/701* (2013.01); *A61F 2002/704* (2013.01); *A61F 2002/741* (2013.01); *Y10T 74/20207* (2015.01); *Y10T 74/20348* (2015.01)

(56) References Cited

U.S. PATENT DOCUMENTS

| | | | | |
|---|---|---|---|---|
| 5,728,172 | A  * | 3/1998  | Krieger | A61F 2/644 602/26 |
| 6,223,604 | B1   | 5/2001  | Fronczak et al. | |
| 6,673,117 | B1 * | 1/2004  | Soss et al. | 623/24 |
| 7,361,192 | B2 * | 4/2008  | Doty | A61F 2/4425 623/17.11 |
| 7,597,017 | B2 * | 10/2009 | Bedard et al. | 73/866.4 |
| 7,823,460 | B2 * | 11/2010 | White | A61F 2/468 73/804 |
| 8,020,503 | B2 * | 9/2011  | Ekholm et al. | 112/475.08 |
| 8,156,824 | B2 * | 4/2012  | Schulz | A61F 2/468 73/862.08 |
| 8,805,662 | B2   | 8/2014  | White | |
| 8,973,460 | B2 * | 3/2015  | Duplouy | B25J 17/0266 74/490.01 |
| 2003/0005786 | A1 * | 1/2003 | Stuart | B23Q 1/5462 74/479.01 |
| 2004/0177701 | A1  | 9/2004 | Zubok et al. | |
| 2007/0051180 | A1  | 3/2007 | White | |
| 2008/0257057 | A1  | 10/2008 | Habeger et al. | |
| 2009/0082867 | A1 * | 3/2009 | Sebastian Bueno | A61F 2/4425 623/17.16 |
| 2011/0118878 | A1  | 5/2011 | White | |

OTHER PUBLICATIONS

International Search Report and Written Opinion in International Application No. PCT/US2011/060599, 8 pages, mailed Jun. 12, 2012.
"Implants for surgery—Wear of total intervertebral spinal disc prostheses—Part 2: Nucleus replacements", *International Standard*, ISO 18192-2 (12 pages) (Jun. 15, 2010).
"In-Cylinder Linear Transducer", *Penny + Giles* Data Sheet ICT050 (4 pages) (Feb. 2009).
"The three-degree-of-freedom planar parallel manipulator", University of Pretoria pp. 88-120 (No date given).
"Transforming Axis of Rotation in X, Y, θ System", Galil Motion Control, Inc., (Application Note #2415) (No date given).
Adelstein, B.D., et al., "Kinematic Design of a Three Degree of Freedom Parallel Hand Controller Mechanism", Proceedings *of the ASME Dynamic Systems and Control Division*, DSC-vol. 58: 539-546 (1996).
Awtar, S., "Synthesis and Analysis of Parallel Kinematic XY Flexure Mechanics", Unpublished Doctoral Dissertation, Massachusetts Institute of Technology (Feb. 2004).
Bonev, I.A., et al., "Changing Assembly Modes without Passing Parallel Singularities in Non-Cuspidal 3-RPR Planar Parallel Robots", *Proceedings of the Second International Workshop on Fundamental Issues and Future Research Directions for Parallel Mechanisms and Manipulators* (Sep. 21-22, 2008).
Briot, S., et al., "Self-Motions of General 3-RPR Planar Parallel Robots", *The International Journal of Robotics Research*, 27(7): 855-866 (Jul. 2008).
Chablat, D. and Staicu, S., "Kinematics of a 3-PRP Planar Parallel Robot", *UPB Scientific Bulletin*, Series D: Mechanical Engineering, 71(2): 3-15 (2009).

Chandra, R., et al., "Solving the Forward Kinematics of the 3RPR Planar Parallel Manipulator using a Hybrid Meta-Heuristic Paradigm", *Proceedings of the 8th IEEE International Conference on Computational Intelligence in Robotics and Automation*, pp. 177-182 (Dec. 15-18, 2009).
Dwarakanath, T. A., et al., "In-Parallel Passive Compliant Coupler for Robot Force Control", Paper presented at Proceedings of the ASME Mechanisms Conference, Baltimore, MD (Sep. 2000).
Eppinger, S.D. and Seering, W.P., "Understanding Bandwidth Limitations in Robot Force Control", MIT Artificial Intelligence Laboratory (A.I. Memo No. 948) (Aug. 1987).
Fujie, H., et al., "Forces and Moments in Six-DOF at the Human Knee Joint: Mathematical Description for Control", *J. Biomechanics*, 29(12): 1577-1585 (1996).
Fujie, H., et al., "The Use of Robotics Technology to Study Human Joint Kinematics: A New Methodology", *J. of Biomechanical Engineering*, 115: 211-217 (Aug. 1993).
Gosselin, C., et al.,"A Planar parallel 3-DOF cable-driven haptic interface ", *Proceedings of the 12$^{th}$ World Multi-Conference on Systemics, Cybernetics and Informatics*; Jointly with the 14$^{th}$ International Conference on Information Systems Analysis and Synthesis; WMSCI, 6 pages (2008).
Haage, M. et al., "Reconfigurable Parallel Kinematic Manipulator for Flexible Manufacturing" Presented at 13$^{th}$ IFAC Symposium on Information Control Problems in Manufacturing, Moscow, Russia, pp. 145-150 (Jun. 3-5, 2009).
Hollerbach, J.M., "Forward Kinematics for Position" (Sep. 2004).
Husty, M. L. "Non-Singular Assembly Mode Change in 3-RPR-parallel Manipulators", In *Computational Kinematics*, Kccskcmcthy et al., eds. pp. 51-60 (2009).
Jiang, Q. and Gosselin, C.M., "Geometric Optimization of Planar 3-RPR Parallel Mechanisms", *Transactions of the Canadian Society for Mechanical Engineering*, 31(4): 457-468 (2007).
Jiang, Q. and Gosselin, C.M., "Geometric Synthesis of Planar 3-RPR Parallel Mechanisms for Singularity-Free Workspace", *Transactions of the Canadian Society for Mechanical Engineering*, 33(4): 667-678 (2009).
Joshi, A. R., "Design and Control of a Three Degree-of-Freedom Planar Parallel Robot", Unpublished master's thesis, Russ College of Engineering and Technology, Ohio University, Athens, OH (Aug. 2003).
Kong, X., "Forward Kinematics and Singularity Analysis of a 3-RPR Planar Parallel Manipulator", In *Advances in Robot Kinematics: Analysis and Design*, Lenarcic, J. et al. eds. (Netherlands: Springer Science+Business Media B.V) pp. 29-38 (2008).
Lee, J.D., et al., "Computer Simulation of a Parallel Link Manipulator", *Robotics and Computer-Integrated Manufacturing*, 5(4): 333-342 (1989).
Liu, X-J. and Kim, J., "A New Spatial Three-DoF Parallel Manipulator With High Rotational Capability", *IEEE/ASME Transactions on Mechatronics*, 10(5): 502-512 (Oct. 2005).
Liu, Y., et al., "Modelling and control of a parallel redundant manipulator with hydraulic actuators", Proceedings of the Institute of Mechanical Engineers, Part I, Journal of Systems and Control Engineering, 220(3): 211-221 (May 1, 2006).
Martinez, L. and Hayes, M.J.D., "CUSP Kinematic Model Development", *Proceedings of the 19$^{th}$ Canadian Congress of Applied Mechanics* (Jun. 2003).
Muller, A., "Redundant Actuation of Parallel Manipulators", In *Parallel Manipulators, Towards New Applications 6*, Wu, H. ed. (Vienna, Austria: I-Tech Education and Publishing), pp. 87-108 (Apr. 2008).
Ottaviano, E. and Ceccarelli, M., "Optimal Design of Capaman (Cassino Parallel Manipulator) With Prescribed Workspace", Laboratory of Robotics and Mechatronics DiMSAT—University of Cassino, Cassino, FR Italy.
Refaat, S., et al., "Asymmetrical three-DOFs rotational-translational parallel-kinematics mechanisms based on Lie group theory", *European Journal of Mechanics—A/Solids*, 25(3): 550-558 (May 2006).
Roy, J. and Whitcomb, L.L., "Adaptive Force Control of Position/Velocity Controlled Robots: Theory and Experiment", IEEE Transactions on Robotics and Automation , 18(2): 121-137 (Apr. 2002).

(56) References Cited

OTHER PUBLICATIONS

Rudy, T.W., et al., "The effect of the point of application of anterior tibial loads on human knee kinematics", *J. of Biomechanics*, 33: 1147-1152 (2000).

Satya, S.M., et al., "Hybrid Control of a Planar 3-DOF Parallel Manipulator for Machining Operations", *Technical Report, Department of Mechanical and Industrial Engineering, University of Urbana-Champaign, Urbana, Illinois USA* (1995).

Sugar, T.G. and Kumar, R.V., "Design and Control of a Compliant Parallel Manipulator", *Journal of Mechanical Design*, 124(4): 676-683 (Dec. 2002).

Taghirad, H.D., "MECH 573: Mechanics of Robotics systems", Department of Mechanical Engineering, McGill University, Montreal, Quebec, Canada (2006).

Tyler, C.M. "In-Parallel Passive Compliant Coupler for Robot Force Control", Unpublished master's thesis, University of Florida, FL (2000).

Walker, P.S., et al. "A Knee Simulating Machine for Performance Evaluation of Total Knee Replacements," *J. Biomechanics*, 30(1): 83-89, (1997).

Walker, P.S., et al. "Methodology for Long-Term Wear Testing of Total Knee Replacements," *Clinical Orthopaedics and Related Research*, 1(372):290-301 (2000).

Wang, Y., "Symbolic Kinematics and Dynamics Analysis and Control of a General Stewart Parallel Manipulator", Unpublished master's thesis, State University of New York at Buffalo, Buffalo, NY (2008).

Wenger, P. and Chablat, D., "Definition sets for the Direct Kinematics of Parallel Manipulators", *Advanced Robotics*, pp. 859-864 (Jul. 7-9, 1997).

Wenger, P., and Chablat, D., "Kinematic analysis of a class of analytic planar 3-RPR parallel manipulators", Paper presented at International Workshop on Computational Kinematics, Duisburg: Germany (2009).

White, B., et al., "Multiaxis Joint Simulator with Software Implemented Soft Tissue Simulation," *Proceedings from the Materials & Processes for Medical Devices Conference*, Sep. 8-10, 2003, Anaheim, California, ASM International, pp. 240-243.

Williams II, R.L. and Joshi, A.R., "Planar Parallel 3-RPR Manipulator", Paper presented at the Proceedings of the Sixth Conference on Applied Mechanisms and Robotics, Cincinnati, OH (Dec. 12-15, 1999).

Williams II, R.L. and Shelley, B.H., "Inverse Kinematics for Planar Parallel Manipulators", Paper Presented at 1997 ASME Design Technical Conferences, Sacramento, CA, pp. 1-6, (Sep. 14-17, 1997).

Zhang, B. "Design and Implementation of a 6 DOF Parallel Manipulator With Passive Force Control", Unpublished doctoral dissertation, University of Florida, Gainesville, FL (2005).

White, B.F., et al., "A Simulator Study of TKR Kinematics Using Modeled Soft-Tissue Constraint: Virtual Soft-Tissue Control for Knee Simulation," *Journal of ASTM International*, 3(8) [online] (2006) [retrieved on May 15, 2013]. Retrieved on the Internet URL: http://www.astm.org.

International Preliminary Report on Patentability in International Application No. PCT/US2011/060599, "Method and Apparatus for Joint Motion Simulation," mailed May 30, 2013.

* cited by examiner

METHOD AND APPARATUS FOR JOINT MOTION SIMULATION

RELATED APPLICATION

This application claims the benefit of U.S. Provisional Application No. 61/413,873, filed on Nov. 15, 2010.

The entire teachings of the above application are incorporated herein by reference.

BACKGROUND OF THE INVENTION

Prosthetic implant failure mechanisms are numerous. Among the most prevalent causes of failure are polyethylene wear, loosening, infection, and mal-alignment. Polyethylene wear comprises the largest single identifiable cause of implant failure today. Moreover, polyethylene wear can predispose implants to loosening as a result of increased loading of the reformed tissues. As implant technology evolves, new and more complex modes of wear, damage, and failure are being identified. As a consequence of these facts, there is a great need for rigorous implant life cycle testing in simulator machines that are capable of replicating the subtleties of human motion.

Simulator machines address the implant longevity problem by providing a non-human environment in which new and existing prosthetic devices are evaluated using accelerated life testing. These machines allow researchers to isolate and study design deficiencies, identify and correct materials problems, and ultimately provide physicians and patients with longer life prosthetic systems. Simulator machines approximate human joint motion. Clearly, the closer the approximations of human joint motion, the more reliable are the results.

SUMMARY

The present invention is generally directed to apparatus and methods for joint motion simulation that provide enhanced motion control to a prosthetic simulator. The prosthetic simulator provides a non-human environment in which to evaluate new and existing prosthetic devices, particularly implantable prosthetic devices, through accelerated life testing.

A joint motion simulator to simulate biomechanical motion includes a mount to which a prosthetic device is mounted, actuators coupled to the mount to drive the mount, and a programmable controller to drive the actuators to translate the mount and to rotate the mount with a center of rotation controllable independent of translation.

The actuators may include at least three linear actuators, which can be coupled to a sleeve, e.g., the outer sleeve of a vertical (Z axis) actuator, and may be displaced vertically along the sleeve. The controller may be programmed to vary the center of rotation with linear translation and rotation of the mount. The joint motion simulator may further include displacement sensors that measure displacement of the actuators and the controller may drive the actuators based on the measured displacement. In some embodiments, the actuators include linear actuators and the displacement sensors include length sensors. The center of rotation or axis of rotation can be an instant center of rotation.

In one embodiment, a joint motion simulator to simulate a biomechanical motion includes a mount to which a prosthetic device is mounted and at least three linear actuators coupled to the mount to rotate and translate the mount.

In addition to the at least three linear actuators, the joint motion simulator may further include a linear actuator to translate the mount in a linear direction substantially parallel to the axis of rotation. The linear actuator to translate can include a piston within a sleeve, the piston being coupled to the mount and being hydraulically driven to translate the mount, and the at least three linear actuators can be coupled to the sleeve. Further, the linear actuator to translate can include a second piston coupled to the mount, the first and second pistons being driven in opposite directions. Each of the at least three linear actuators may include a piston hydraulically driven in a cylinder, the piston being coupled through a pin joint to the sleeve.

A joint motion simulator to simulate biomechanical motion may include a mount to which a prosthetic device is mounted; actuators coupled to the mount to drive the mount; and a programmable controller to drive the actuators to rotate the mount about an axis, to translate the mount in lateral directions relative to the axis of rotation and to laterally translate the axis of rotation independent of translation of the mount.

A method of driving a prosthetic device to stimulate joint motion includes driving the prosthetic device in rotation along an axis of rotation and moving the axis of rotation laterally in multiple directions.

The prosthetic device can be mounted to a mount, in which case driving the prosthetic device in rotation can include driving actuators coupled to the mount to rotate the mount. In one embodiment, at least three linear actuators are coupled to the mount. The method of driving the prosthetic device may further include driving the actuators to translate the mount in lateral directions relative to the axis of rotation. The axis of rotation, in turn, may be moved laterally independent of translation of the mount. In some embodiments, the method of driving the prosthetic device further includes sensing displacement of the actuators and driving the actuators can include driving the actuators based on the sensed displacement. The actuators may include linear actuators and sensing displacement may include sensing length of the linear actuators. In an embodiment, the method of driving the prosthetic device further includes driving the prosthetic device in translation in a linear direction substantially parallel to the axis of translation.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF THE INVENTION

A description of example embodiments of the invention follows.

Figure 1A:
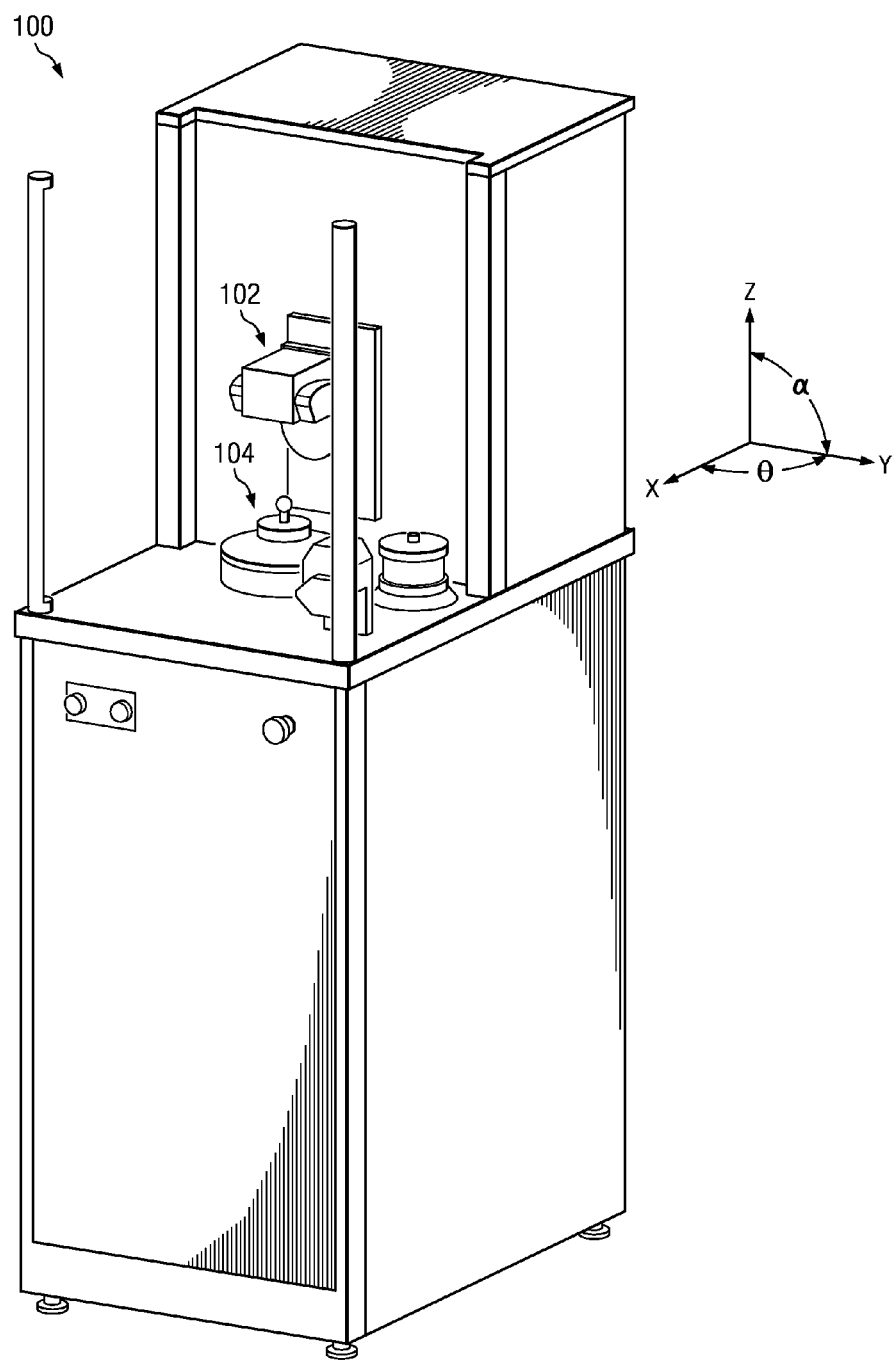
FIG. 1A illustrates a prosthetic simulation system according to one embodiment of the invention.

FIG. 1A illustrates a simulation system 100 embodying the present invention. As with prior systems, one element of the joint is mounted into an upper mount 102 and the other element of the joint is mounted to a lower mount (platform) 104. The lower mount 104, also referred to herein as the specimen stage or mechanical stage, is controllable with X-Y-Z-θ degrees of freedom.

Figure 1B:
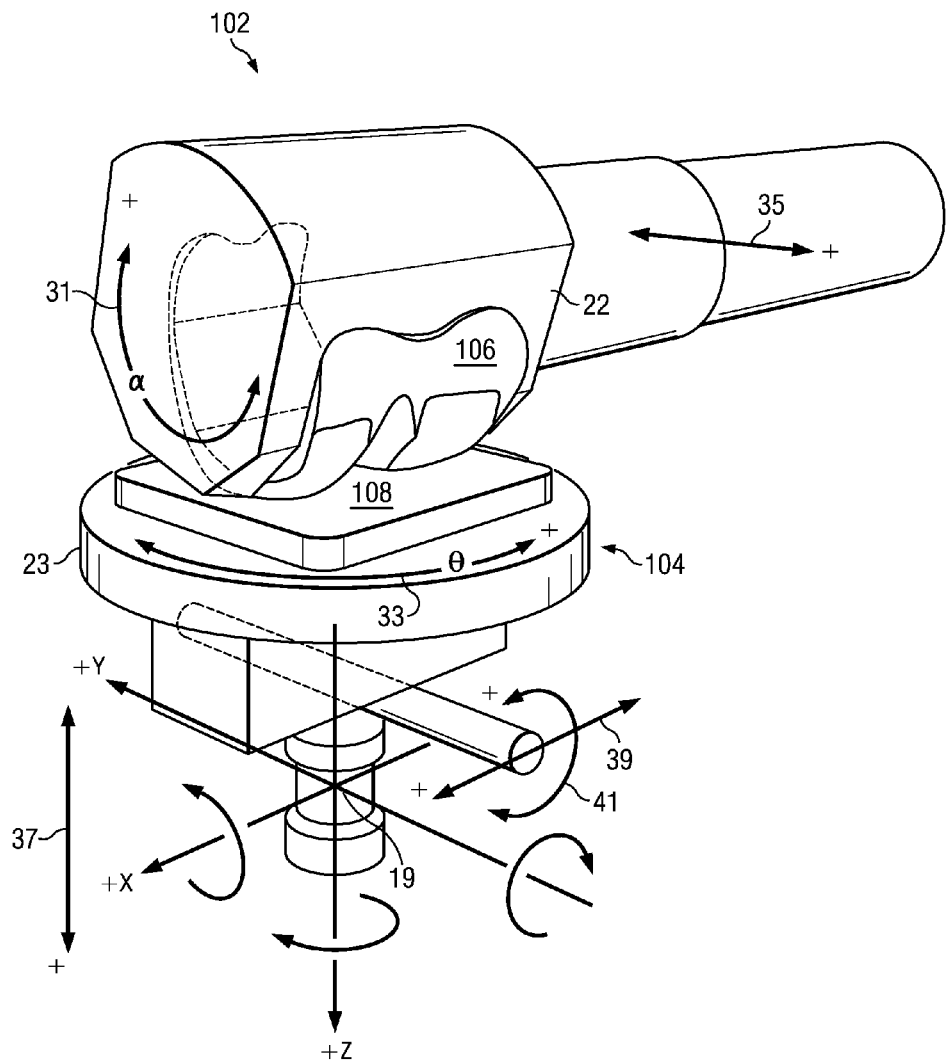
FIG. 1B is a schematic illustration of a prior art simulator stage for a prosthetic device.

FIG. 1B illustrates a prosthetic knee joint, though the system can carry prosthetic elements of any joint. The joint elements 106, 108 butt against each other between the two mounts and are separately driven through a programmed motion. A prior simulation system is described in the U.S. Pat. No. 7,823,460 to Bruce F. White, which is incorporated by reference in its entirety. In the prior simulation system, the upper mount was moveable by actuators in the lateral Y direction 35 and was also rotatable 31 about a front to rear axis X with the angle α. The lower platform was moveable in the Z axis 37 and was also rotatable 33 about the vertical Z axis through an angle θ. In the prior system uncontrolled degrees of freedom include translation 39 and rotation 41 of the lower platform.

The prior simulator includes a multi-axis force/torque transducer 19 mounted beneath a tibial tray 23 of the simulator stage so that the three components of femoral-tibial contact force (and moment) can be monitored. Transducer 19 can be a six-channel strain gauge transducer. In addition, the prior simulator can include one or more position sensors or transducers to measure the relative translational and rotational positions of the femoral 22 and tibial 23 components of the simulator. As shown in FIG. 1B, the position sensor can monitor the flexion/extension angle 31, internal/external (IE) rotation angle 33, anterior/posterior (AP) translation 35, and vertical (compression/distraction) position 37 of the prosthesis. The medio-lateral (ML) knee translation 39 and varus valgus rotation 41 can also be monitored.

Although the combined motions of the prior simulation system allow for complex relative movement between the two joint elements for wear testing, they are not able to completely simulate the normal biological movement. In particular, the prior system does not control relative movement along the X axis. Further, the rotational axes are fixed; whereas, in the body, the axis of rotation may be displaced from the center and may even move through action of the joint. The present invention allows for control in each of the X, Y and Z axes as well as rotational movement in the angle θ about a center of rotation that itself can move along the X and Y axes. Although not initially implemented in the upper mount 102, the invention could be similarly applied to that mount to allow for movement of the center of rotation of the angle α.

A goal of a joint simulator is to achieve and/or control the right, e.g., anatomically correct, contact kinematics among rigid bodies, e.g., the prosthetic joint elements. To this end, embodiments of the present invention provide independent programmatic control of the center of rotation in two orthogonal axes without relative translation of the contacting rigid bodies. Throughout this specification, the term center of rotation and axis of rotation is used interchangeably.

In rigid body mechanics, the term instantaneous center of rotation can apply to a velocity (instant) center of rotation and to an acceleration center of rotation. A velocity center of rotation is typically defined relative to a fixed or global reference frame. Take for example a wheel rolling on a planar surface, the surface being fixed relative to the global reference frame. The wheel's motion can be described as a translation in a direction parallel to the planar surface and a contemporaneous rotation about the center of the wheel. At any given point in time, the acceleration center of rotation is at the center of the wheel while the velocity (instant) center of rotation is at the point of contact with the surface. In another example, a shaft rotates about a fixed axis, e.g., the center axis of the shaft. Here, the velocity center of rotation is the same as the acceleration center of rotation at any given point in time. Thus, the instantaneous center of rotation of the exemplary shaft is both the velocity (instant) and acceleration center of rotation.

Figure 1C:
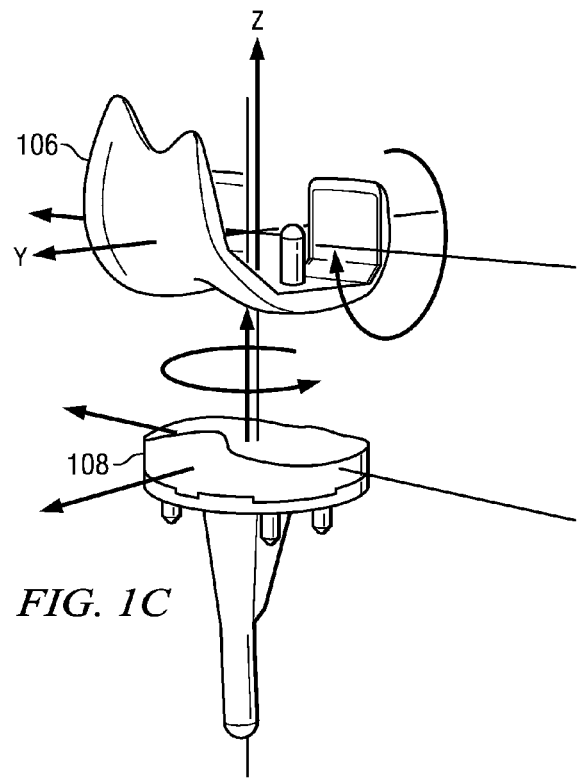
FIGS. 1C-1F illustrate potential motion of joint elements of a prosthetic knee.
Figure 1D:
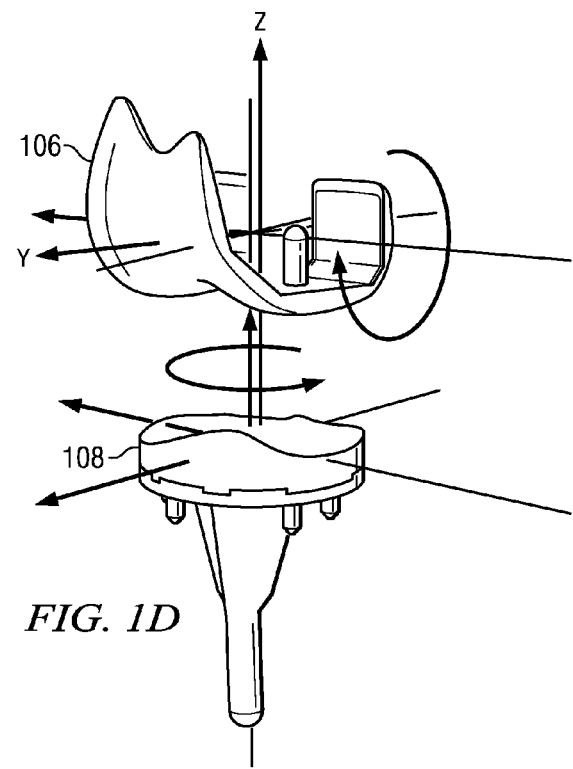
Figure 1E:
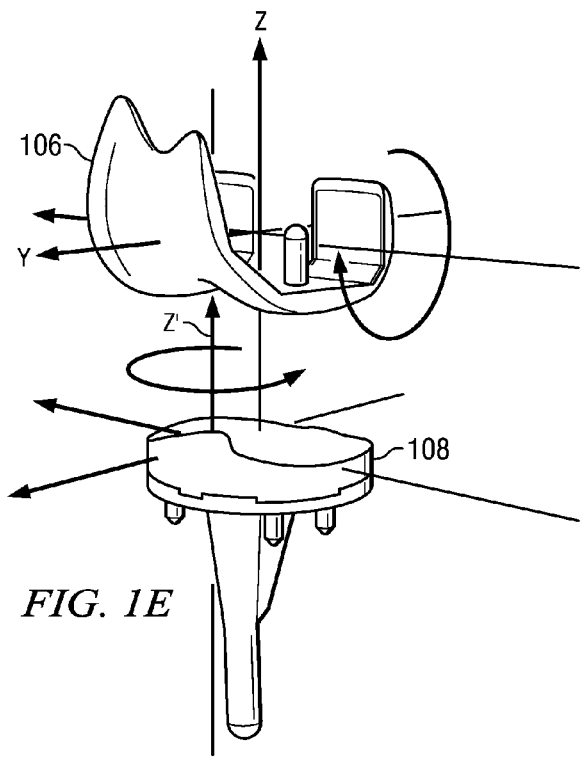
Figure 1F:
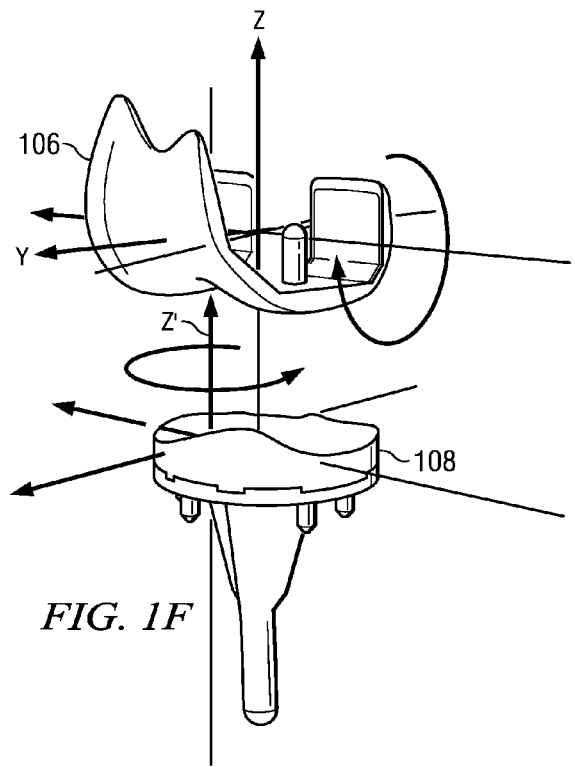

FIGS. 1C-F illustrate potential motion of joint elements 106, 108 of a prosthetic knee. FIGS. 1C and 1D illustrate rotation of the lower tibial element 108 about the normal fixed Z axis of the system. FIGS. 1E and 1F illustrate translation of the center of rotation of the lower tibial element 108, such that the tibial element rotates about an axis Z' other than the normal Z axis of the system. The Z' axis is an instant center of rotation. The described prior art only allows for the motion of FIGS. 1C-1D, not the motion of FIGS. 1E-1F.

Figure 2:
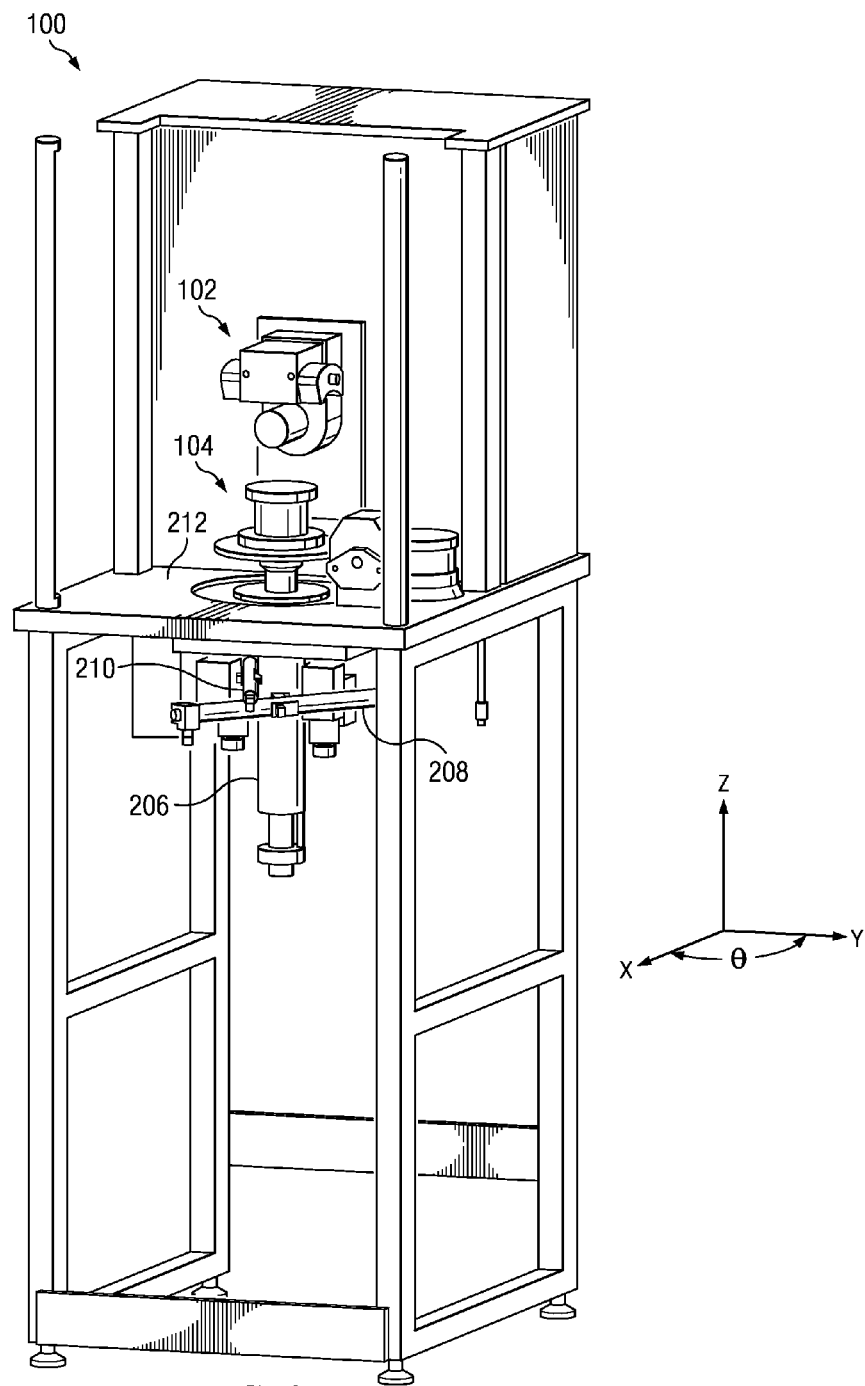
FIG. 2 illustrates the system of FIG. 1A with part of the lower cabinet and a hydraulic fluid system removed.

FIG. 2 illustrates the system of FIG. 1A with the lower cabinet and a hydraulic fluid collection system removed to illustrate components embodying the present invention. In FIG. 2 can be seen a Z axis actuator 206 which results in vertical movement of the lower platform 104. Also illustrated are two of three X-Y-θ actuators 208 and 210 mounted below simulator table top 212. As will be described in detail below, the three X-Y-θ actuators drive the sleeve of the Z axis actuator in the X and Y directions, and also rotate the sleeve through the angle θ about a center of rotation that may be displaced in the X and Y directions.

Figure 3:
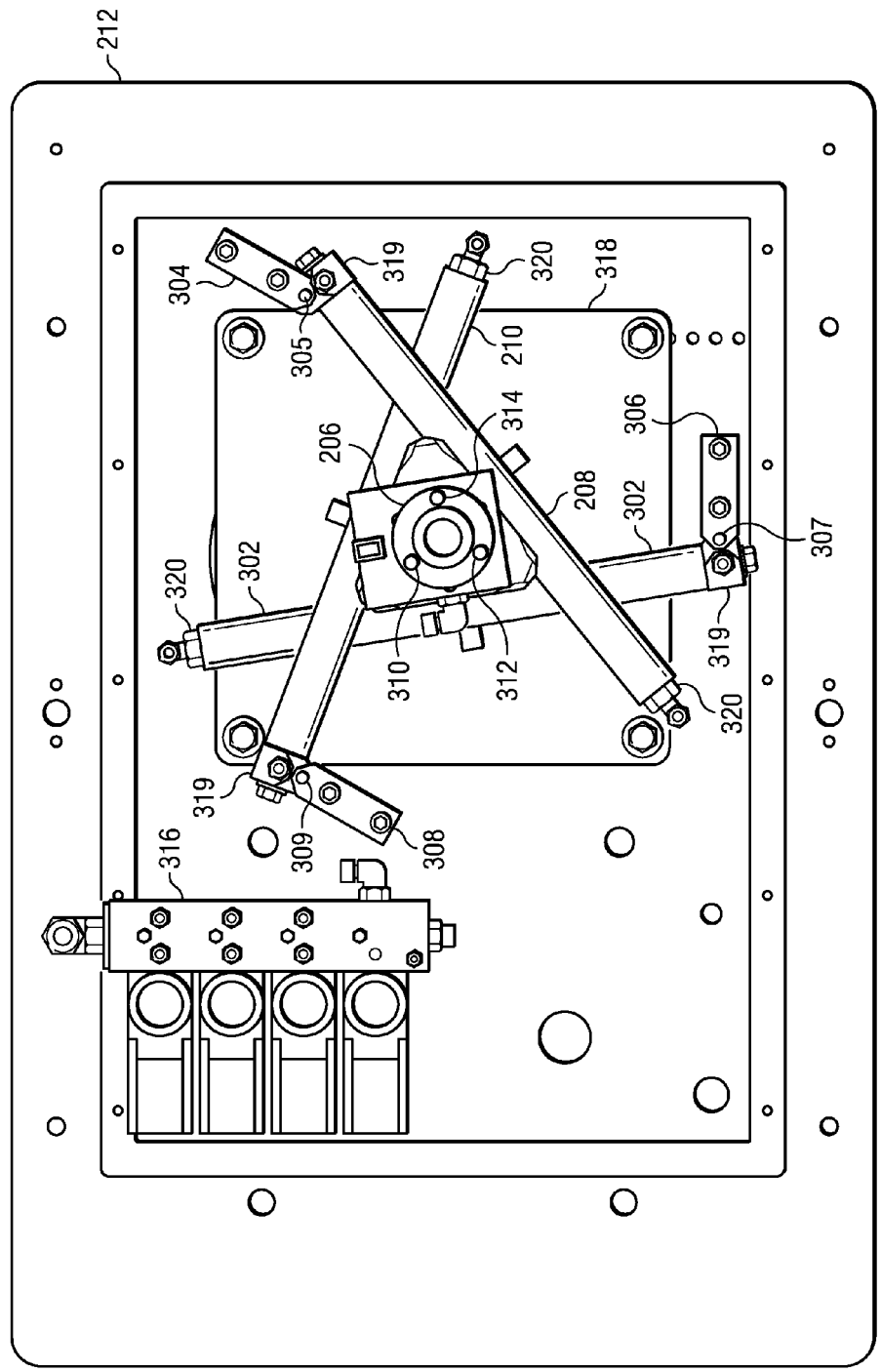
FIG. 3 is a view of three x-y-θ actuators viewed from below.

FIG. 3 is a view of the three X-Y-θ actuators 208, 210 and 302 as viewed from below. As will be discussed in detail below, each actuator includes a drive piston pinned to the vertical actuator sleeve. Each of the actuators 208, 210 and 302 is mounted to the bottom of table top 212. For example, actuator 208 is mounted through a support post 304 to the bottom of the table, actuator 302 is mounted through a support post 306 to the bottom of the table, and actuator 210 is mounted through a support post 308 to the bottom of the table. As shown, the actuators 208, 210 and 302 are coupled to the support posts via pins 305, 307, and 309, respectively. Thus, each actuator includes a pinned end 319 and a free end 320.

The actuators can be connected to hydraulic valve manifold 316 via suitable hydraulic conduits (not shown). A controller can drive each actuator by sending a drive signal to the valves of valve manifold 316. Although actuators 208, 210, and 302 are described herein as being hydraulically driven, it will be understood that other types of controllable actuators can be used as the X-Y-θ actuators. In general, three or more independently and interdependently linear or rotary actuators may be used to produce X-Y translation and angular rotation in θ.

Figure 4:
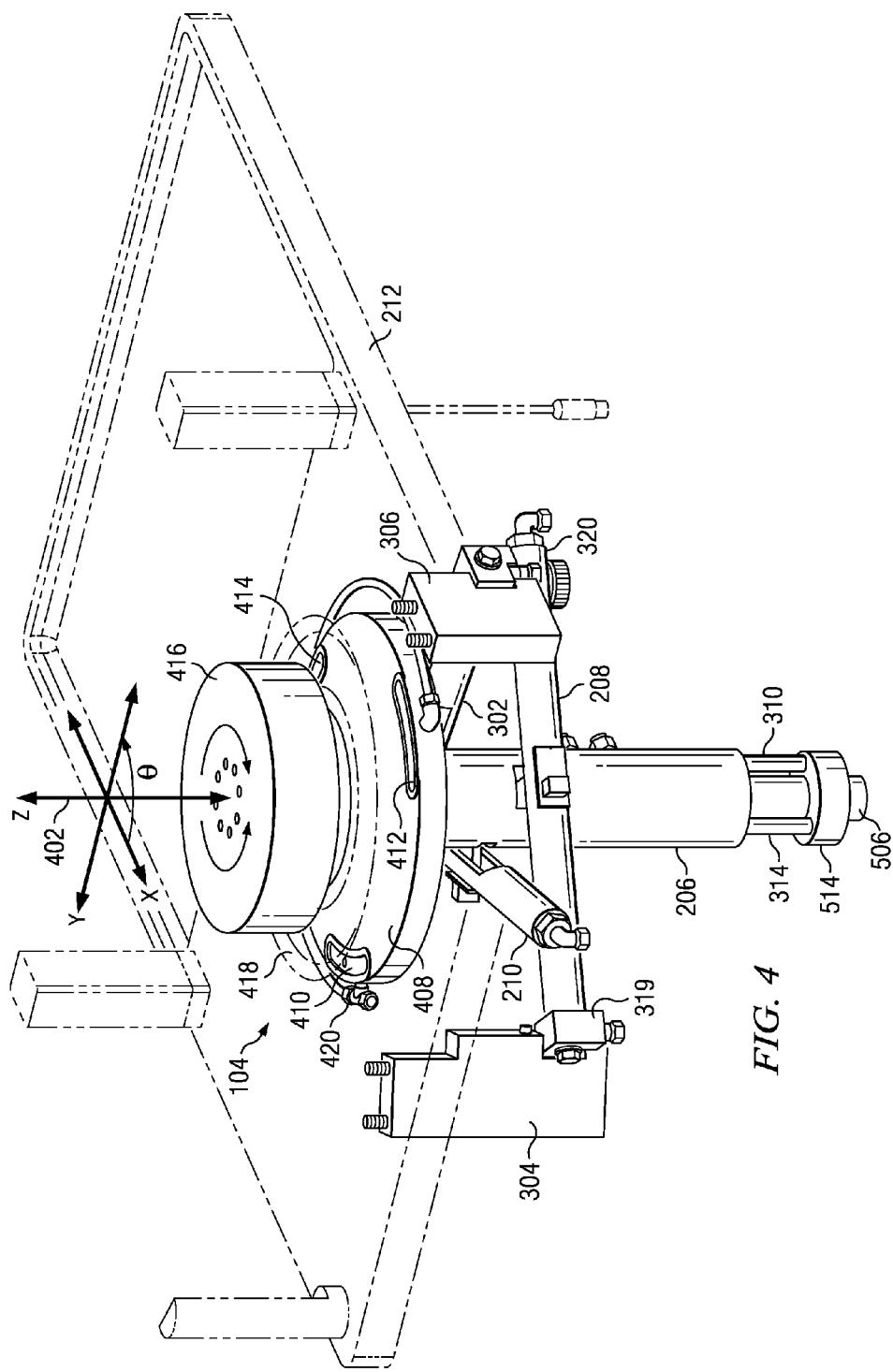
FIG. 4 illustrates detail of a lower platform actuator assembly.

FIG. 4 illustrates further detail of the lower platform actuator assembly. Motion diagram 402 shows translation in the x, y, z direction and rotation θ about a center of rotation of lower mount 104. The outer sleeve of the vertical actuator 206 is mounted to a hydrostatic bearing plate 408 which butts up against the bottom of the table top 212 and is supported by a plate 318 suspended below the table top. In each of its upper and lower surfaces, bearing plate 408 includes three oval ports 410, 412 and 414 through which hydraulic fluid is expressed to form the hydrostatic bearing. In this way, the expressed hydraulic fluid can create a hydrostatic film on the upper 409 and lower (not shown) surfaces of bearing plate 408. Hydrostatic fluid is provided to ports 410, 412 and 414 through feed tubes 420. The joint element support platform or specimen plate 416 is coupled to the Z axis actuator through an opening (612 in FIG. 6C) in the table top 212 as will be discussed below. Table top 212 can include a gutter 418 adjacent the opening in table top 212.

Figure 5:
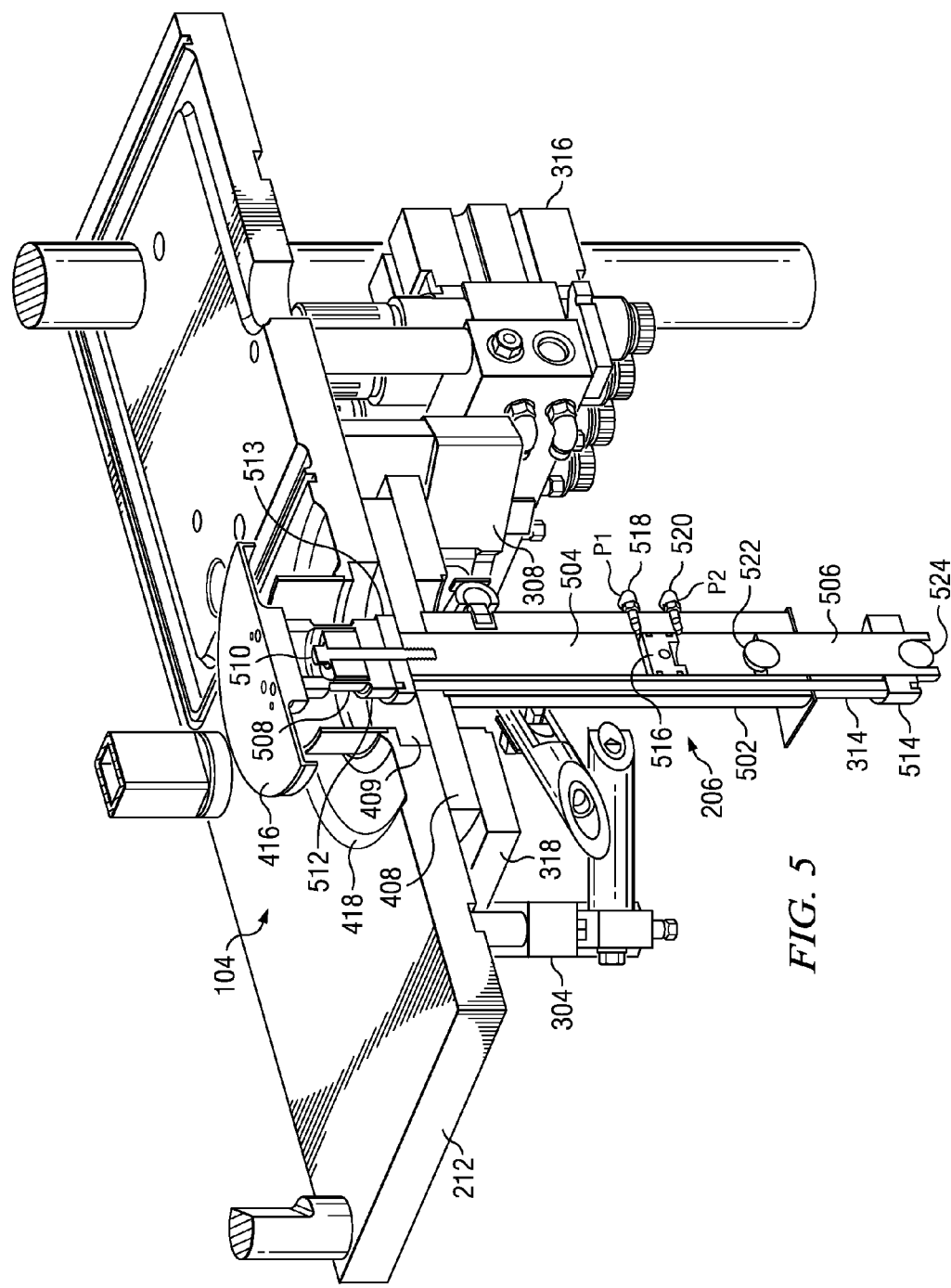
FIG. 5 is a partial cut-away view of the lower platform actuator assembly.
Figure 6A:
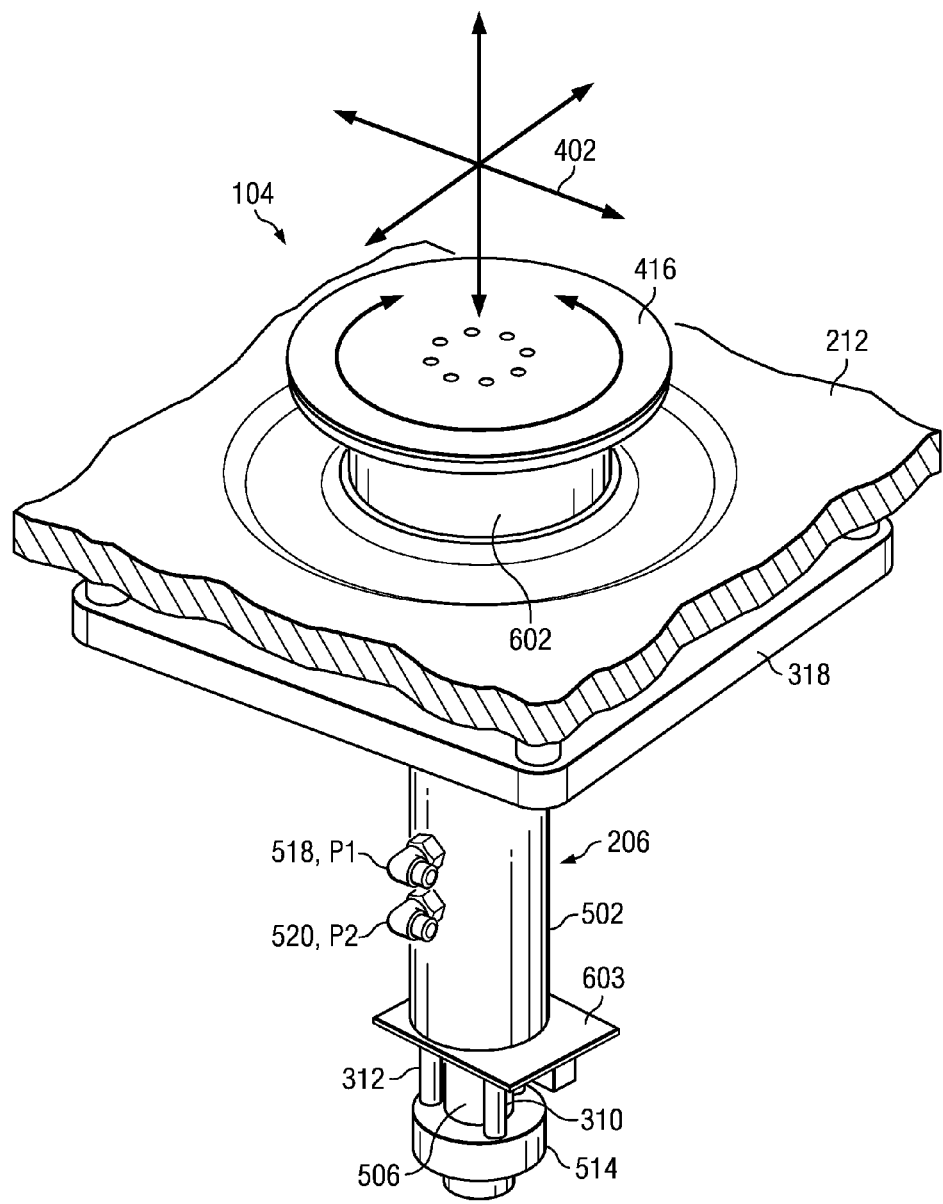
FIG. 6A is a partial, perspective view of the lower platform actuator assembly illustrating a vertical actuator according to an embodiment of the invention.
Figure 6B:
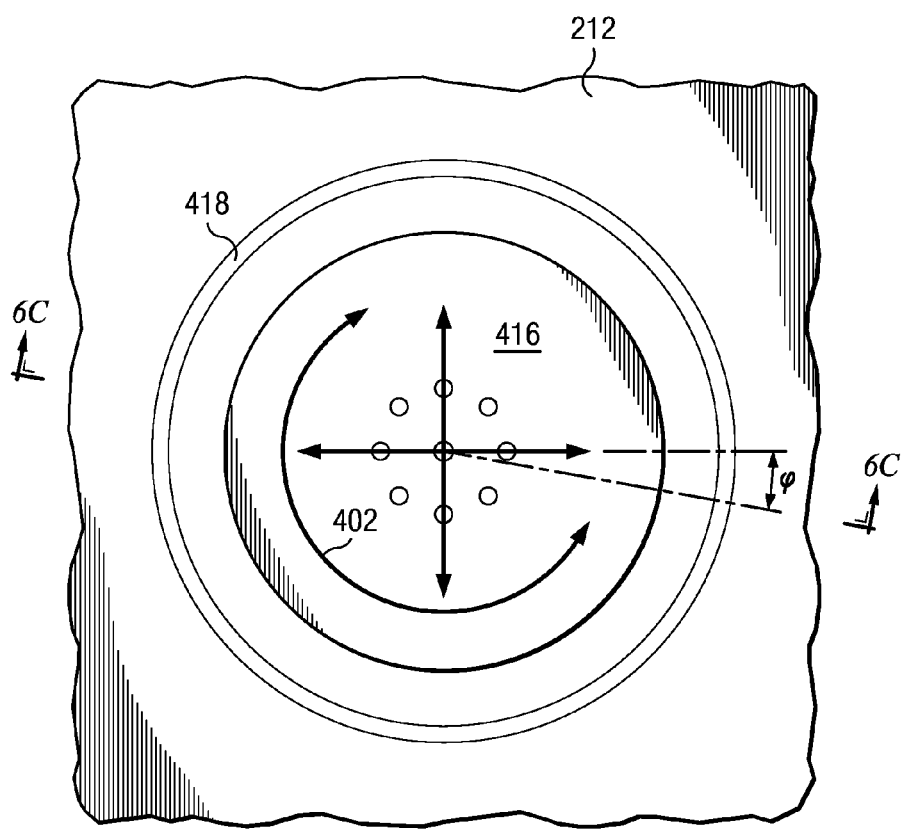
FIG. 6B is a top view of the lower platform actuator assembly of FIG. 6A.
Figure 6C:
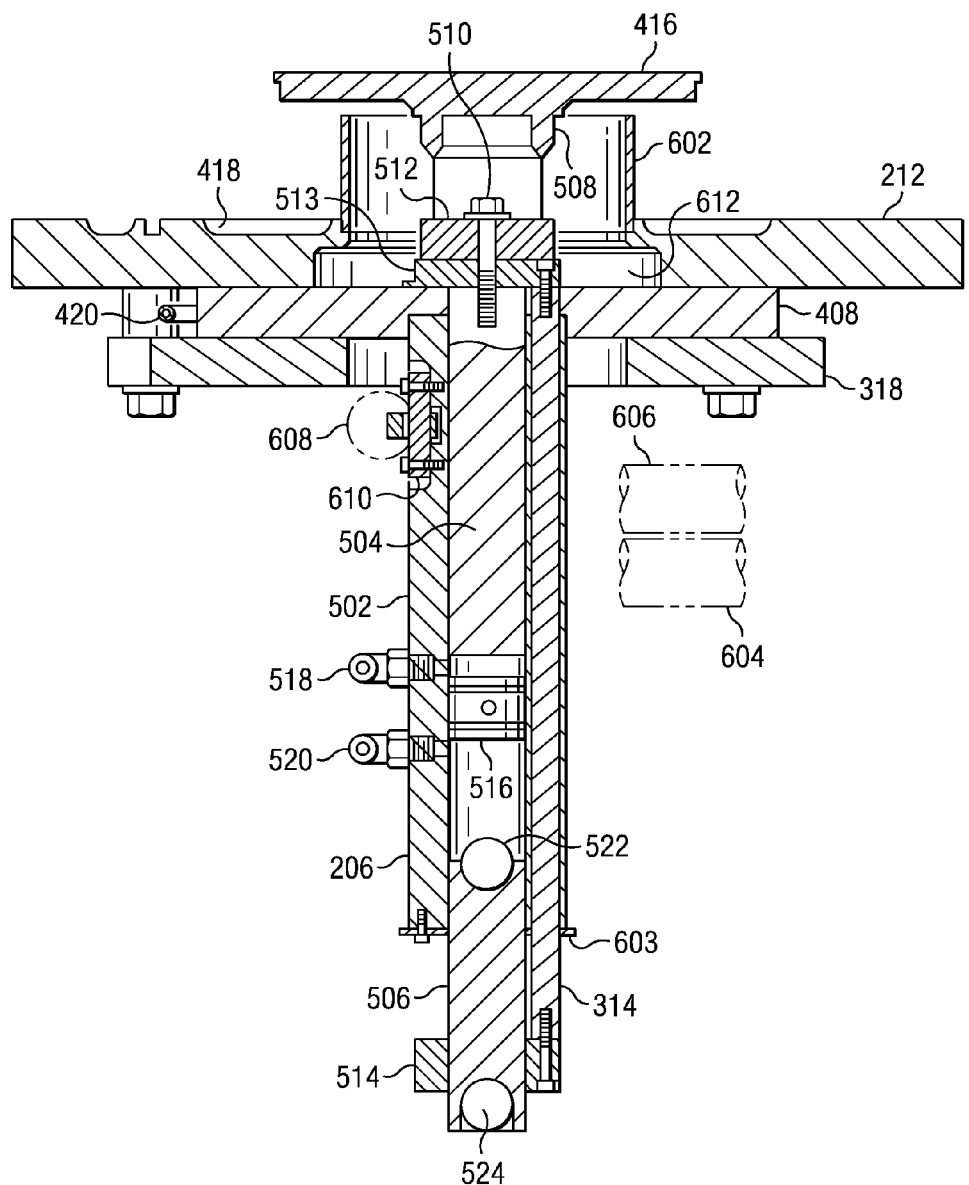
FIG. 6C is a cross-sectional view of the lower platform actuator assembly of FIG. 6A as indicated in FIG. 6B.

Details of the vertical actuator 206 can be seen in FIGS. 5 and 6A-C, as well as FIG. 4. FIG. 5 is a partial cut-away view of the lower platform actuator assembly. FIGS. 6A-C are perspective, top, and cross-sectional views, respectively, of the lower platform actuator assembly with actuators 208, 210 and 310 removed for clarity. The vertical actuator 206 includes an outer sleeve 502 in which two hydraulically driven pistons 504 and 506 are positioned. Each of the pistons 504, 506 is directly coupled to the specimen platform 416 through a load sensor 508. The load sensor 508 senses forces in three orthogonal linear directions and three orthogonal moments about those axes. Because the prosthetic joint element to be tested mounts to specimen platform 416, which is mounted to load sensor 508, the load sensor can be used to monitor forces and moments acting at the joint element. The load sensor 508 can be a six-channel strain gauge transducer, such as transducer 19 described with reference to FIG. 1B. The piston 504 is coupled to the transducer plate 512 directly through a pin 510. The lower piston 506 is coupled to the same plate 512 through upper guide plate 513 and through three rods 310, 312 and 314 that extend through the sleeve 502 from a ring (lower guide plate) 514 fixed to the lower piston 506.

A plug 516 is fixed to the sleeve 502 between the pistons 504 and 506. Hydraulic fluid is introduced to the space between the plug 516 and piston 504 through a port 518 at pressure P1. Separately, hydraulic fluid at pressure P2 is introduced to the space between the plug 516 and piston 506 through a port 520. It can be seen then that the hydraulic fluid at pressure P1 presses upwardly against the piston 504 to drive the specimen platform 416 upwardly; whereas, the pressure P2 drives the piston 506 downwardly to move the specimen platform downwardly through the rods 310, 312 and 314. The differential between pressures P1 and P2 determines whether the specimen platform moves upward, downward or not at all, with the pistons moving together through their common connection, the plate 512. Lower piston 506 includes magnets 522 and 524 that magnetically couple to a Hall effect sensor for vertical displacement sensing of the piston assembly and specimen mount.

As shown in FIG. 6C, vertical actuator 206 is coupled to specimen platform 416 through load sensor 508, the coupling extending through opening 612 in table top 212. The positions of actuators 208, 210 and 302 relative to vertical actuator 206 are shown in FIGS. 4 and 5 and, in phantom at 604, 606 and 608 in FIG. 6C. The actuators 208, 210 and 302 are displaced vertically along sleeve 502 of vertical actuator 206. As illustrated by phantom 608, actuator 302 is coupled to sleeve 502 of vertical actuator 206 through a bracket and a pin 610 that extends along the Z axis. Similarly, actuators 208 and 210 are each coupled to sleeve 502 though a bracket and a pin (see FIGS. 4 and 5) at a level corresponding to the location of phantoms 606 and 604, respectively.

Also shown in FIGS. 6A and 6C is isolation tube 602 attached to table top 212 and surrounding load sensor 508. The isolation tube provides a shield against contamination of the lower actuator assembly with fluids and lubricants that can arise from cadaveric testing and wear testing. PC board 603 attached to the bottom of sleeve 502 can include control circuitry for Z axis actuator 206, such as for vertical displacement sensing.

Figure 7:
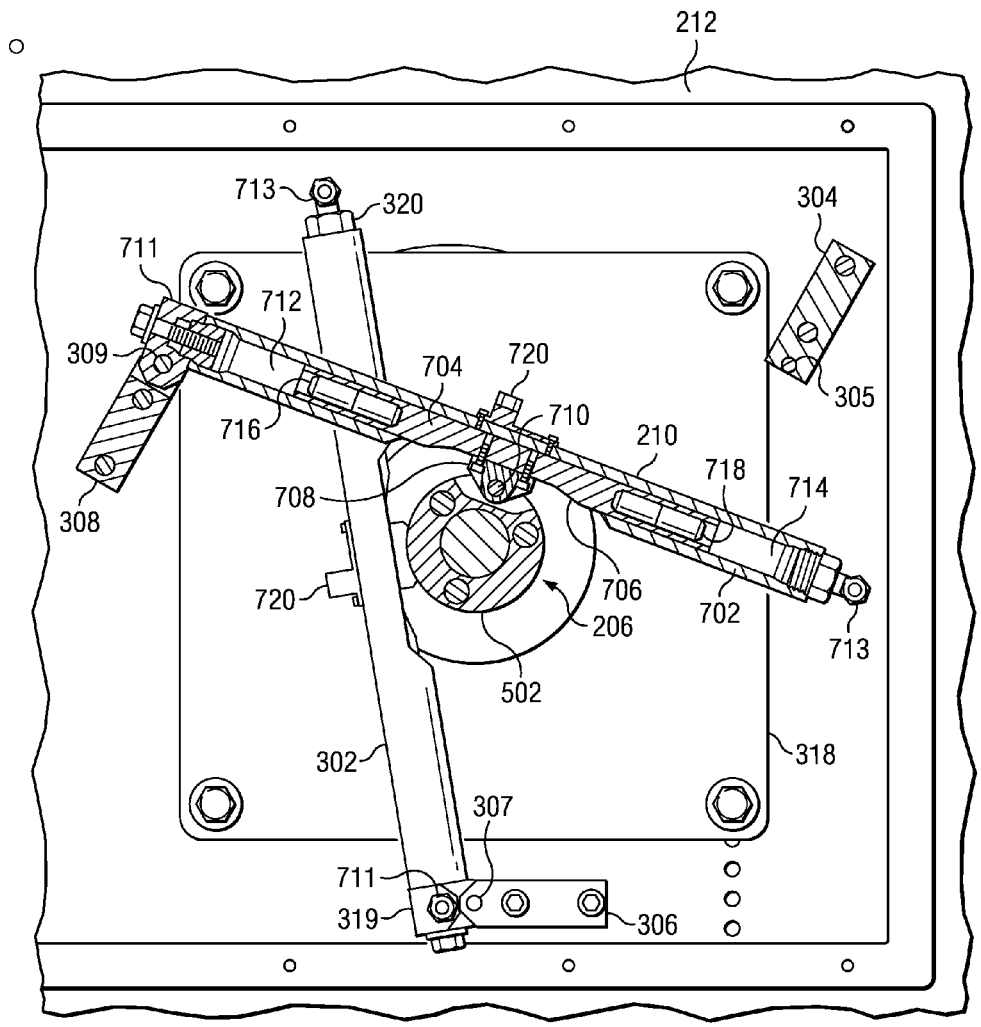
FIG. 7 illustrates further detail of one of the three x-y-θ actuators of FIG. 3.

FIG. 7 illustrates detail of one of the three X-Y-θ actuators, it being understood that the three actuators are identical but displaced angularly by 120 degrees and displaced vertically along the sleeve 502 to prevent interference with each other.

As shown, the actuator 210 includes a single piston 704 within an outer cylinder 702. The cylinder 702 is pinned at one end to support post 308 through a pin 309 that extends along the Z axis. The other end of cylinder 702 is free. The cylinder 702 is cut away along a length adjacent to the vertical actuator 206 to expose the piston and enable it to be coupled to the sleeve 502 of the vertical actuator through a bracket 708 and a pin 710 that extends along the Z axis. The piston itself is cut away (706) at the bracket 708 to allow for a more compact assembly.

Hydraulic fluid is applied at distinct pressures through oil ports (fittings) 711 and 713 to oil volumes 712 and 714 at opposite ends of the piston within the cylinder 702. The differential pressure volumes cause the piston to move along its axis and apply a force through the pin 710 to the sleeve or cylinder 502 of the Z axis actuator. Magnets 716 and 718 are embedded at opposite ends of the piston 704 and are sensed by Hall effect sensors mounted to a bracket 720 on the cylinder 702 for sensing displacement of the piston 704 within cylinder 702. By sensing displacement of the piston, length of the actuator, e.g., the distance between pin 309 and pin 710, can be sensed. A controller can then drive the actuators based on the sensed length or change in length.

As will be described in greater detail below, the combined linear movement of the three pistons in linear actuators 208, 210 and 302 results in movement in any X-Y direction and rotation through the angle θ about any center of rotation within an allowable range of the system. For example, if each piston were driven towards a respective mounting post with equal displacement, the sleeve 502 would rotate about a center axis in a counterclockwise direction as viewed in FIG. 7. However, when applying different displacements to the pistons, rotation can be about a different axis and X-Y movement can be imposed. As another simple illustration, if the pistons in each of actuators 208 and 302 (see FIG. 3) are driven toward the actuator 210, as no force is applied to piston 210, the Z actuator sleeve 502 and thus the specimen would move in the direction toward the pin 708 of actuator 210.

A detailed mathematical analysis of the control of the X-Y-θ movement is presented below. The analysis is derived from the work of Atul Ravindra Joshi, "A Design and Control of a Three Degree-Of-Freedom Planar Parallel Robot," Masters Thesis, Ohio University, August 2003, incorporated by reference in its entirety. However, the analysis has notably been extended to incorporate a parameter $r^O$ to allow for control of the axis of rotation. Further, the Joshi work is directed to a robot; there is no suggestion of its use in a system for prosthetic joint motion simulation.

The control system used in this simulator may be an extension of that disclosed in U.S. patent application Ser. No. 12/942,886, by Bruce F. White, filed Nov. 9, 2010, incorporated by reference in its entirety. A specific implementation is presented below. With the controller, the center of rotation is controllable and infinitely variable within a range independent of X-Y translations of the mount.

Displacement Control

Inputs to the system of actuators (called a planar actuator array) include translations, rotation and constraints. These inputs are:

1) x and y translations;
2) angular rotation; and
3) constraints, e.g., the x, y position of the axis of rotation.

Constraint of the axis of rotation is necessary mathematically in order to unambiguously differentiate between rotation and translation. A translation may be considered a rotation about an axis at infinity. An x translation would be a rotation about an axis at y infinity, where a y translation would be a rotation about an axis at x infinity. The usual formulation of a rotational transformation is about the origin (i.e., 0,0).

In an actuator system according to the principles of the present invention, the axis of rotation can be chosen to be anywhere within a range of x and y positions—so then it is chosen to be somewhere (constrained) in order to compute the desired extensions (displacement lengths) of each of the actuators.

Intuitively it seems easier to define the axis of rotation relative to a fixed global coordinate system. However, in the natural knee this axis is more 'naturally' associated with the long axis of the tibial shaft. In an actuator system according to an embodiment of the present invention, the tibial plateau translates, and hence the long axis of the tibial shaft translates, which makes the more desirable presentation an axis that moves relative to the fixed global system.

Under displacement control, the control problem can be considered as two mathematical processes: 1) composition of the actuator drive signals from the input set point signals, and 2) decomposition of the measured position and orientation into components which may be compared to the set point signals, or to the actuator drive signals, to determine the current tracking error. The inputs to the system, which include the set point x and y positions, the set point angular rotation and the chosen x, y coordinates of the center of rotation, are referred to as the input set point signals. The actuator drive signals include the individual signals provided as inputs to each of the control loops that can be used to provide, for example, a valve drive signal for hydraulically driven actuators. The valve drive signal differs from the actuator drive signal in that it has been determined from one or more measures of error (e.g., x-y position error) and has been acted on by the control process.

Returning to the two components of the control problem, mathematically, rotations are taken about the origin. In rigid body mechanics, when the coordinates of a reference frame embedded in the rigid body (at the desired center of rotation) relative to a global coordinate system are known, a rotation can be applied to the rigid body. The body can be translated to the origin using those known coordinates, then rotated, then translated back to the original position (of the center of rotation). In a planar system, a single angle and two linear coordinates are sufficient to solve the problem. Since the coordinates of each of the actuator attachment points relative to the embedded coordinate system are known, and given that their initial positions were known relative to a global system, the transformed coordinates of each attachment point may be determined. From these coordinates unique extension lengths of each of the individual actuators may be determined.

Returning to the second part of the control problem, if the actuator extensions (lengths) are measured locally then these measurements may be used directly for feedback control of the simulator. Otherwise, a global measurement system that determines three parameters for the rigid body may be used. Angle and x, y coordinates of the center of rotation can provide a natural means of providing feedback. These measurements can be treated in much the same manner as the set point signals to determine a set of unique actuator extensions, which can then be used as feedback signals to the control channels.

Force Control

Under force control, one can specify desired forces and torques, then drive the actuators of the simulator stage or machine to achieve these forces and torques. Inputs to the system of actuators include forces, torque and constraints. The inputs are:

1) x and y force;
2) torque; and
3) the x, y position of the axis of rotation, or other constraints that guide rotation.

As with the displacement control paradigm, constraint of the axis of rotation is necessary. One may consider current machine designs as well as the natural knee. Current machine designs impose a fixed axis of rotation or a translating axis of rotation. In either case, the bearing systems for rotation provide reaction forces which balance the actuator applied forces.

Under force control, the center of rotation can be established from calculated forces and torques, e.g. based on ligaments and joint surfaces. The center of rotation may also be based on sensed forces and torques, e.g. forces and torques sensed by a multi-axis sensing element such as load sensor 508 (FIG. 5).

Lower Displacement Stage

An embodiment of a joint motion simulator according to the present invention includes a platform, mount or stage 104 designed to permit three degrees of freedom, namely x and y translations and rotation about an arbitrary axis. As described above with reference to FIGS. 4, 5, and 6A-C, the stage itself can be rigid body constrained to move in a plane by a hydrostatic support system. Motion can be imparted to the stage by three actuators, each coupled to the stage at one end of the actuator and coupled to the machine body at the other end, although coupling need not occur at the actuator ends (see e.g., FIG. 3). At each attachment point, the actuators may be coupled to the machine body or the stage with a revolute joint having an axis normal to the plane of motion.

Mathematical Analysis

Figure 8:
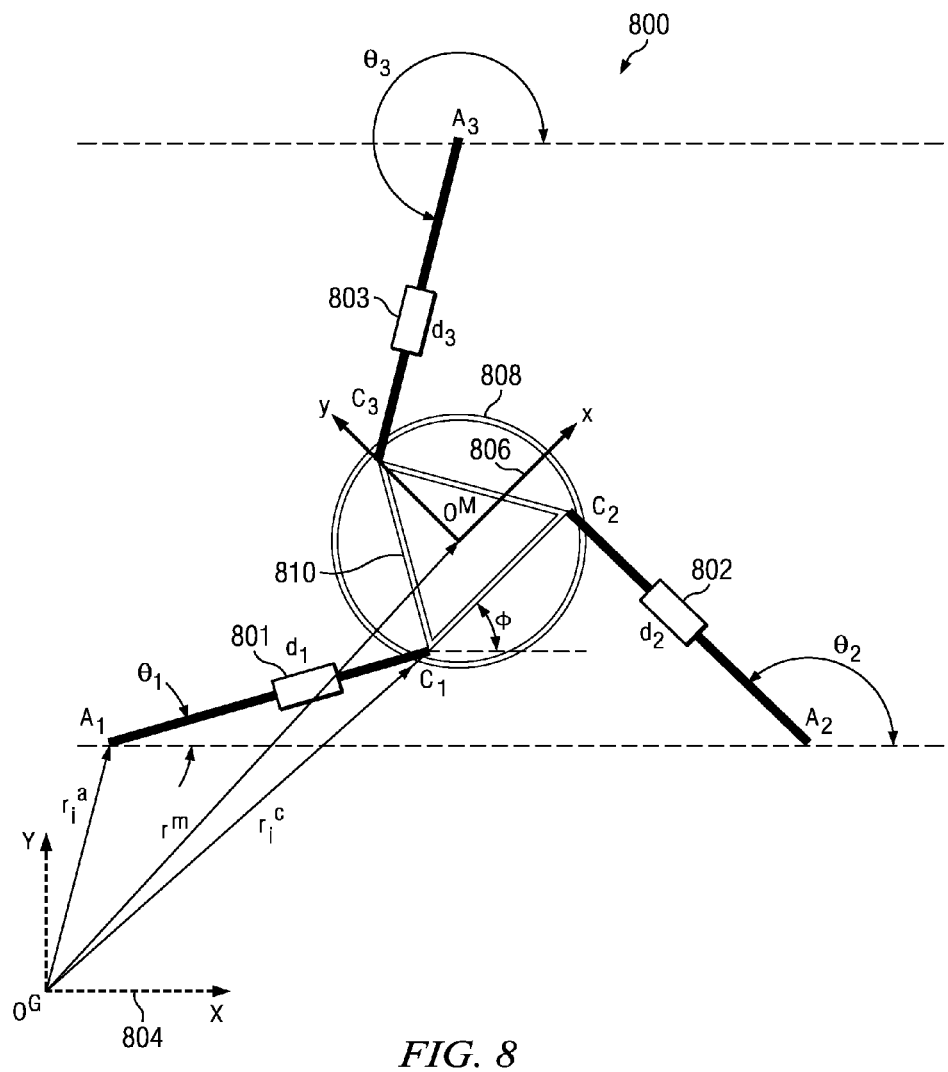
FIG. 8 is a schematic illustration of a mechanical stage and three actuators used to produce x-y translation and angular rotation about any axis.

Consider a 3RPR planar parallel actuator 800 shown in FIG. 8. The actuator 800 is comprised of three linear actuators 801, 802, 803 with lengths $d_1$, $d_2$ and $d_3$ oriented at corresponding angles $\theta_1$, $\theta_2$ and $\theta_3$ with respect to the x axis of a global reference frame.

A global reference frame 804 is defined with origin at $O^G$ and a movable reference frame 806, attached to the movable stage or mount 808 is defined with origin at $O^M$. The position of $O^M$ relative to $O^G$ is specified by the position vector $r^m$ while the angle of rotation of $O^M$ relative to $O^G$ is defined as $\phi$.

The actuators 801, 802, 803 are attached to the machine frame by revolute joints at each of $A_1$, $A_2$, and $A_3$, while similarly attached to a movable stage 808 by revolute joints at points $C_1$, $C_2$, and $C_3$. Position vectors $r^a_i$ and $r^c_i$ denote the positions of the points $A_i$ and $C_i$ relative to $O^G$ respectively.

A particular pose or configuration 810 of the stage 808 relative to $O^G$ is specified by a pose position vector $r^p$, the orientation angle $\phi$, and a position vector $r^o$ defining the axes of rotation relative to $O^M$ with the stage in the reference position.

Figure 9:
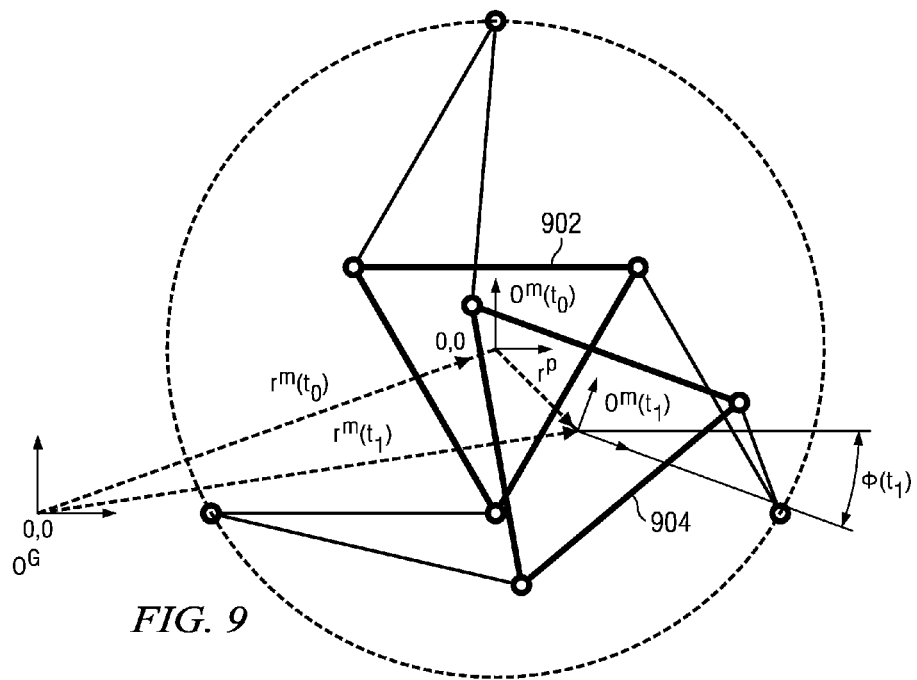
FIG. 9 illustrates how motion of the center of rotation of the mechanical stage can be specified by vector $r^o$ while the orientation of the stage can be specified by angle $\phi$.

FIG. 9 illustrates two successive poses 902 and 904 of the stage 808 at times $t_0$ and $t_1$. The vector representing the translation of the stage is $r^p$ which is the vector difference:

$$r^p = r^m(t_0) - r^m(t_1) \tag{1}$$

where $r^m(t_0)$ and $r^m(t_1)$ represent the positions of the origin of the stage $O^m$ at successive time intervals $t_0$ and $t_1$. The orientation of the stage at successive time intervals (at pose 904 relative to pose 902) is shown as the angle $\phi(t_1)$.

Figure 10:
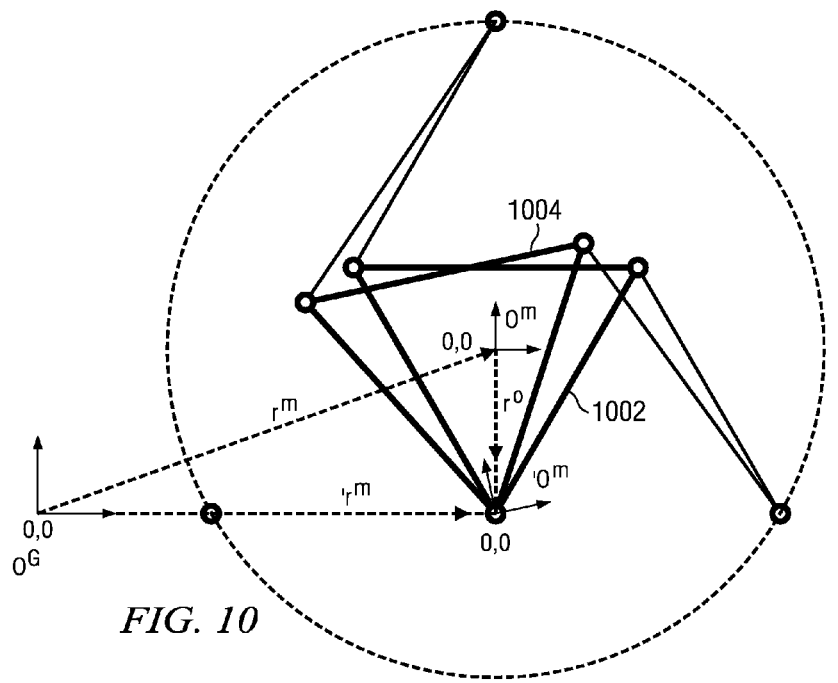
FIG. 10 illustrates how the center of rotation can be specified by vector $r^o$.

FIG. 10 illustrates the vector $r^o$ which can be used to specify the center or axis of rotation relative to the origin of the stage $O^m$. The desired center of rotation is specified in the global coordinate system at $O^G$ as:

$$'r^m = r^m - r^o \tag{2}$$

where $r^m$ represents the positions of the origin of the stage $O^m$. The figure illustrates two poses 1002, 1004 of stage 808. Pose 1004 represents a rotation about the new center of rotation which has been specified to be repositioned from the origin of the stage $O^m$ by an amount $r^o$ resulting in a new center of rotation at $'O^m$. In other words, $'O^m$ is the translated center of rotation as specified by $r^o$. FIG. 10 illustrates that the center of rotation may be programmatically modified by the vector $r^o$.

3RPR actuators have been employed for various purposes and the mathematical solution of both the forward and inverse kinematics has been developed in the literature. The subject analysis is based on the work of Atul Ravindra Joshi, found in his 2003 thesis entitled "A Design and Control of a Three Degree-Of-Freedom Planar Parallel Robot." Several corrections to his reported analysis were required to develop correct forward and reverse kinematics. Joshi credits a paper by R. L. Williams II and B. H. Shelley, "Inverse Kinematics for Planar Parallel Manipulators," Proceedings of DETC '97, ASME Design Technical Conferences, DETC97/DAC-3851, Sacramento, Calif., Sep. 14-17, 1997, pp. 1-6, with a previous solution to this problem.

In a control system for a joint simulator using three linear actuators, the inverse kinematics described below can be used to drive the simulator stage. Once the position or pose of the simulator stage is specified, e.g. the x-y translation, angle of rotation, and position of the center of rotation, the inverse kinematics can calculate the lengths of the linear actuators to achieve that position or pose. The forward kinematics described below can be used to determine the position and/or orientation of the stage, e.g., relative to a global reference frame, given the lengths of the linear actuators. For example, the lengths of the actuators may be sensed using displacement sensors. A controller can then drive the actuators using feedback control based on the sensed length, based on the position of the stage as determined using forward kinematics, or both.

Inverse Kinematics

The inverse kinematics solution determines the requisite lengths $(d_1, d_2, d_3)$ of the three actuator elements to achieve a specified actuator pose, where the pose is specified by $r^p$, $r^o$ and $\phi$.

The five defined position vectors defined above are:

$$r^a_i = \{x^a_i, y^a_i\}$$

$$r^c_i = \{x^c_i, y^c_i\}$$

$$r^m = \{x^m, y^m\}$$

$$r^p = \{x^p, y^p\}$$

$$r^o = \{x^o, y^o\} \tag{3}$$

Where $r^c_i$ are the positions of each of the revolute joints labeled $C_1$, $C_2$ and $C_3$ required to produce the desired pose relative to $O^G$, $r^o$ is the position of the rotational axis relative to $O^M$ and $r^a_i$ are the positions of the revolute joints (the points labeled $A_1$, $A_2$, and $A_3$) attaching the actuators to the global frame $O^G$. The position vector $r^m$ is the position of $O^M$ relative to $O^G$ in the reference position and $r^p$ is the desired displacement of $O^M$ to achieve the desired configuration or pose.

A rotational matrix is defined:

$$R = \begin{bmatrix} \cos\phi & -\sin\phi \\ \sin\phi & \cos\phi \end{bmatrix} \tag{4}$$

Following a displacement of the movable stage the coordinates of each of the revolute joints $C_1$, $C_2$, and $C_3$ are defined as $r^{c'}_i$ which is determined for each point by:

$$r^{c'}_i = ((r^c_i - r^o) \times R) + r^o + r^p \tag{5}$$

The center of rotation position vector $r^o$ is subtracted from the position vector $r^c_i$ for each of the revolute joints before applying the rotational transformation using R. In other words, the position vectors of the revolute joints are first translated to the origin $O^M$ of the stage. Note that it is the addition of the $r^o$ term in equation (5) that permits the programmatic control of the axis of rotation of this system. This is a key feature of the control scheme and is not found expressed in any of the cited references.

The length of each of the three actuators required to achieve the desired pose is calculated:

$$d_i = \sqrt{(r^a_{xi} - r^{c'}_{xi})^2 + (r^a_{yi} - r^{c'}_{yi})^2} \tag{6}$$

Equations (5) and (6) are the inverse kinematic relationships necessary to control the actuator in position control. Independent variables (inputs) are the pose as specified by $r^p$, $r^o$ and $\phi$. The dependent variables (outputs) are $d_i$. Constants of machine design are $r^a_i$ and $r^c_i$.

Forward Kinematics

The solution of the forward kinematics problem determines the current position, $r^p$, and orientation $\phi$ of the stage from the lengths, $d_i$, of the three actuators. The forward kinematics problem is developed from the vector equations expressed in (5) and the length equations expressed in (6). Expansion of (5) and (6) results in three nonlinear equations which must be solved simultaneously.

To simplify the notation the following definitions are adopted. Three points $A_i$ are specified relative to the fixed frame $O^G$, the points $C_i$ are specified relative to the moving frame $O^M$. X and y are the components of the translation of the moving stage and $\phi$ is the rotation of the stage. $L_i$ are the lengths of the extended actuators ($d_i$ earlier). The stage is assumed to rotate about $O^M$.

Three auxiliary terms $B_{1i}$, $B_{2i}$ and $B_{3i}$ are defined:

$$B_{1i} = -2(C_{ix}A_{ix} + C_{iy}A_{iy})$$

$$B_{2i} = 2(C_{iy}A_{ix} - C_{ix}A_{iy})$$

$$B_{3i} = C_{ix}^2 + C_{iy}^2 + A_{ix}^2 + A_{iy}^2 - L_i^2 \quad (7)$$

And the expanded vector relationship (from equations (5) and (6)) is expressed:

$$F_i = x^2 + y^2 + 2(x(C_{ix}c\phi - C_{iy}s\phi - A_{ix}) + y(C_{ix}s\phi + C_{iy}c\phi - A_{iy}) + B_{1i}c\phi + B_{2i}s\phi + B_{3i} \quad (8)$$

In this set of equations, $F_i$ corresponds to three functions (for i=1, 2, 3) corresponding to the kinematic equations for each of the revolute joints of the three actuators affixed to the moving stage. Here, $F_i$ can be considered a dummy variable which is determined by the three equations expressed in equation (8).

The Jacobian is defined:

$$J(X) = \begin{bmatrix} \frac{\delta F_1}{\delta x} & \frac{\delta F_1}{\delta y} & \frac{\delta F_1}{\delta \phi} \\ \frac{\delta F_2}{\delta x} & \frac{\delta F_2}{\delta y} & \frac{\delta F_2}{\delta \phi} \\ \frac{\delta F_3}{\delta x} & \frac{\delta F_3}{\delta y} & \frac{\delta F_3}{\delta \phi} \end{bmatrix} \quad (9)$$

The partial derivatives in (9) are developed from equation (8) as follows:

$$\frac{\delta F_1}{\delta x} = 2(x + C_{ix}c\phi - C_{iy}s\phi - A_{ix}) \quad (10)$$

$$\frac{\delta F_1}{\delta y} = 2(y + C_{ix}s\phi + C_{iy}c\phi - A_{iy})$$

$$\frac{\delta F_1}{\delta \phi} = 2[(x(-C_{ix}s\phi - C_{iy}c\phi)) + (y(C_{ix}c\phi - C_{iy}s\phi)) + (C_{ix}A_{ix} + C_{iy}A_{iy})s\phi + (C_{iy}A_{ix} - C_{ix}A_{iy})c\phi]$$

Equations (7), (8), (9) and (10) are used to formulate an iterative solution to the forward kinematics problem using the Newton-Raphson technique.

Control Approach Example

Figure 11:
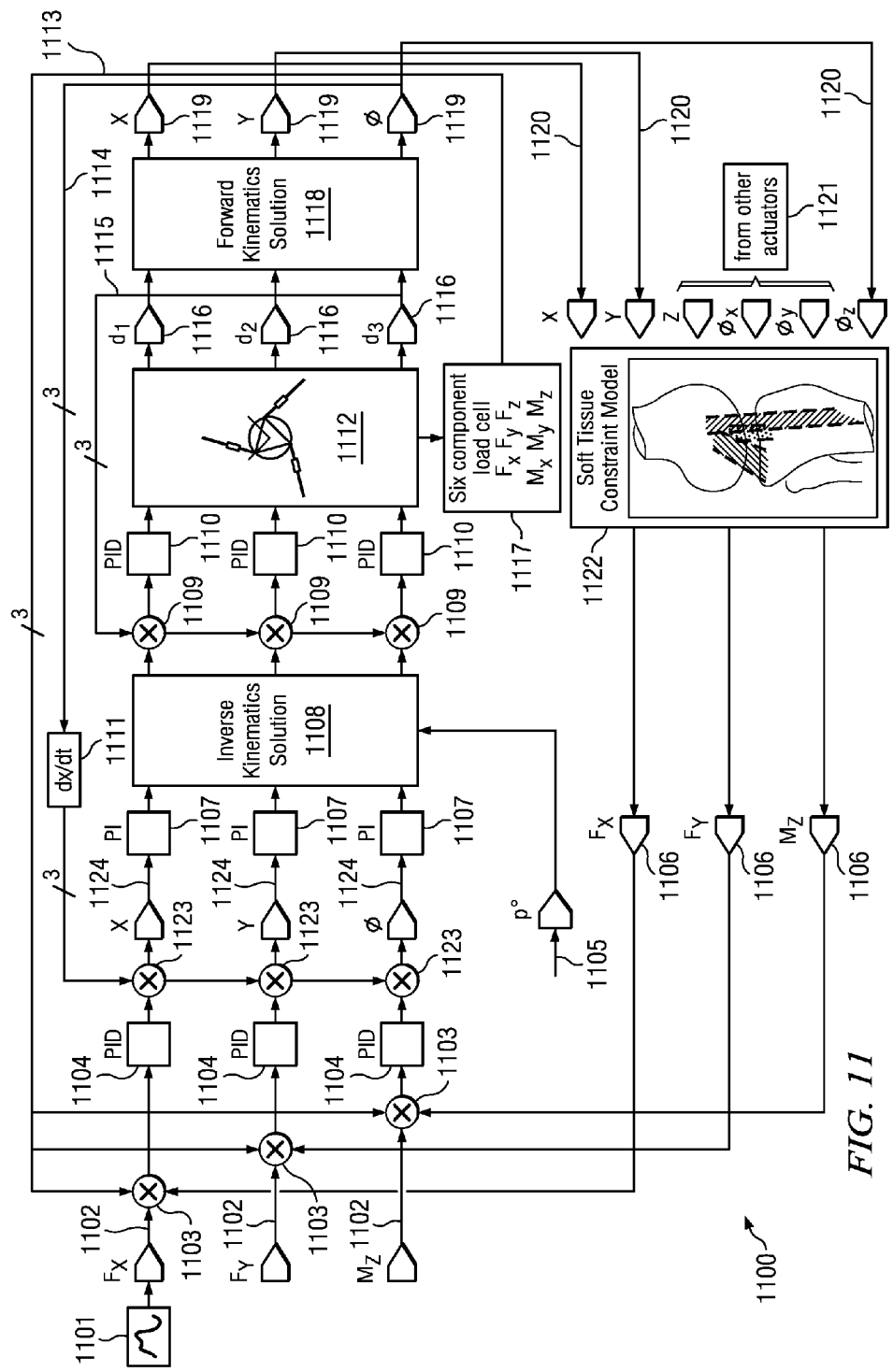
FIG. 11 is a schematic illustration of a control system for a prosthetic simulator according to an embodiment of the invention.

The control system 1100 schematically shown in FIG. 11 illustrates one control approach. Three time series data inputs or reference waveforms 1101 representing two orthogonal forces Fx and Fy and the perpendicular moment Mz, which characterize the active forces of the musculature acting through one cycle of physiologic motion, are recorded by an instrumented orthopedic implant or determined by analytical means. These signals are input to the system at 1102 and represent the desired control action of the control system and actuator. The inputs are summed with one of three feedback signals 1113 at summing junctions 1103. The feedback signals 1113 represent forces and moments measured by the multiaxis load cell 1117, which measures the contact forces of the prosthetic device under test. Also presented at summing junctions 1103 are the calculated constraint forces 1106 determined by the virtual soft tissue constraint model 1122. Both feedback sources 1106 and 1113 are inverted before summing at the summing junction 1103 and therefore the output of the summing junction is an error signal representing the difference between the constraint force and the reference force presented at the system input 1102. The error signals are presented to PID control algorithms 1104, which can be tuned to provide the desired control proportional, integral and derivative gain. Typically only proportional gain will be used at 1104. The output of the PID blocks 1104 are input to one of three summing junctions 1123 where the signals are summed with the time derivative signals calculated at 1111 from one of three feedback sources 1114. These time derivatives represent the linear velocities $V_x$, $V_y$ and the angular velocity $\omega$ of the stage 1112. Summing junctions 1123 calculate a velocity error signal 1124. If the forces and torques are balanced then the outputs of summing junctions 1103 will be zero and the output of the PID control blocks 1104 will likewise be zero and the inputs to summing junctions 1123 will likewise be zero. This will drive the velocity control loop to zero causing movement to cease when the desired force level has been reached. If force equilibrium has not been reached then there will be some net signal applied to summing junctions 1123, which will cause the system to maintain some velocity and hence continue to seek force equilibrium.

The velocity error signals 1124 are presented to PI blocks 1107, which serve to integrate the velocity error to produce a displacement (position, orientation) error. The requisite displacements X, Y and $\phi$ are input to the inverse kinematic solution block 1108, which in turn determines the requisite lengths of each of the three actuators and outputs them to one of three summing junctions 1109. Feedback of the actual length 1115 measured by length sensors in each of the three actuators is inverted and presented to the summing junctions 1109. The length error signal determined at the summing junctions 1109 is input into PID control blocks 1110 where proportional, integral and derivative calculations are performed. The signals from these control blocks are converted to analog drive signals and are used to drive the linear actuators of the actuator system stage 1112. Each actuator length is measured by a linear displacement transducer 1116 and the three outputs are fed to the forward kinematic solution block 1118. The forward kinematic solution block 1118 determines the current position and orientation and outputs the three signals X, Y and $\phi$ 1119. The three output signals 1119 are routed to the derivative calculation blocks 1111 and to the inputs of the soft tissue constraint model 1122.

The soft tissue constraint model 1122 utilizes six inputs, three inputs 1120 originating from this control loop and three inputs 1121 originating from measurement of the displacements of the flexion actuator (e.g., flexion 31 in FIG. 1B) and the vertical position actuator and from measurement of varus valgus rotation (e.g., rotation 41 in FIG. 1B). The soft tissue constraint model 1122 determines the constraint forces that would be supplied by the soft tissue structure and outputs these constraint forces 1106, which are in turn summed with the input drive forces at summing junctions 1103.

The location of the center of rotation of the actuator is provided at input 1105. The center of rotation is expressed as a coordinate pair where: $p^o = \{x^o, y^o\}$. These values may be algorithmically determined or supplied as a pair of time series data expressing the desired center of rotation throughout the programmed motion. The center of rotation values are input into the Inverse Kinematics Solution control block 1108.

Possible Motions

Figure 12A:
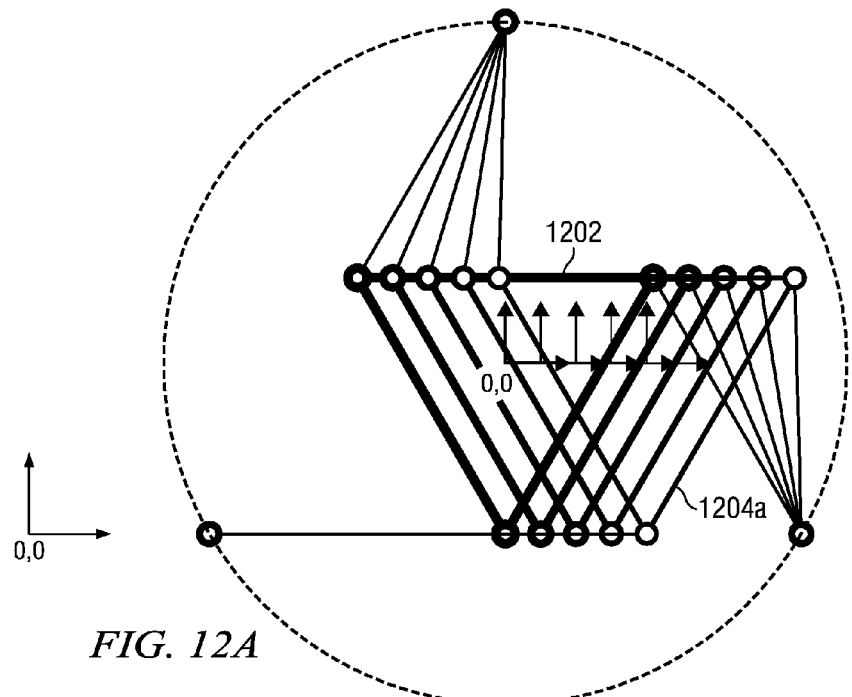
FIGS. 12A-12H illustrate some of the possible motions of the mechanical stage of a prosthetic simulator.
Figure 12B:
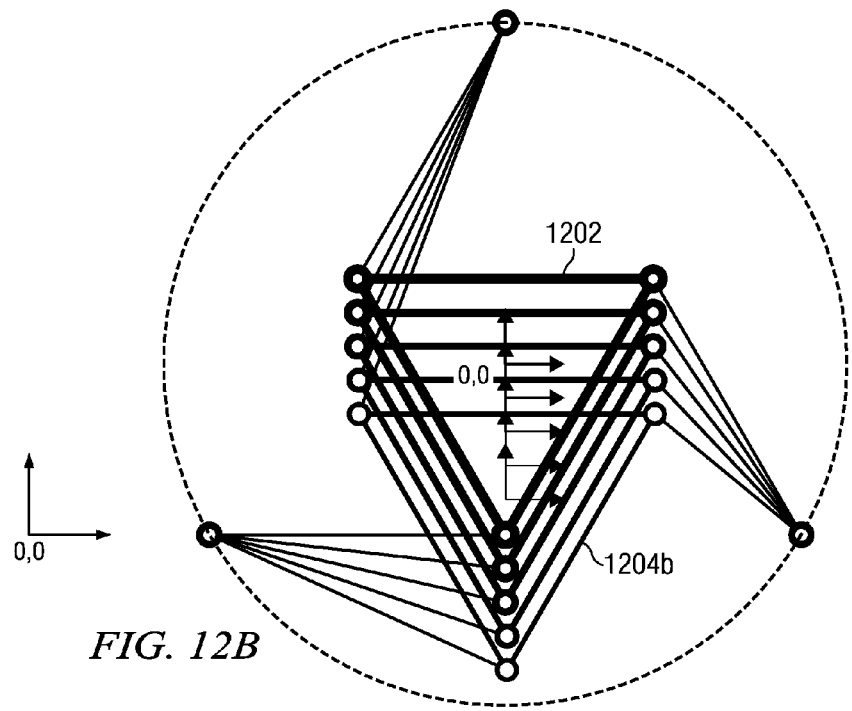
Figure 12C:
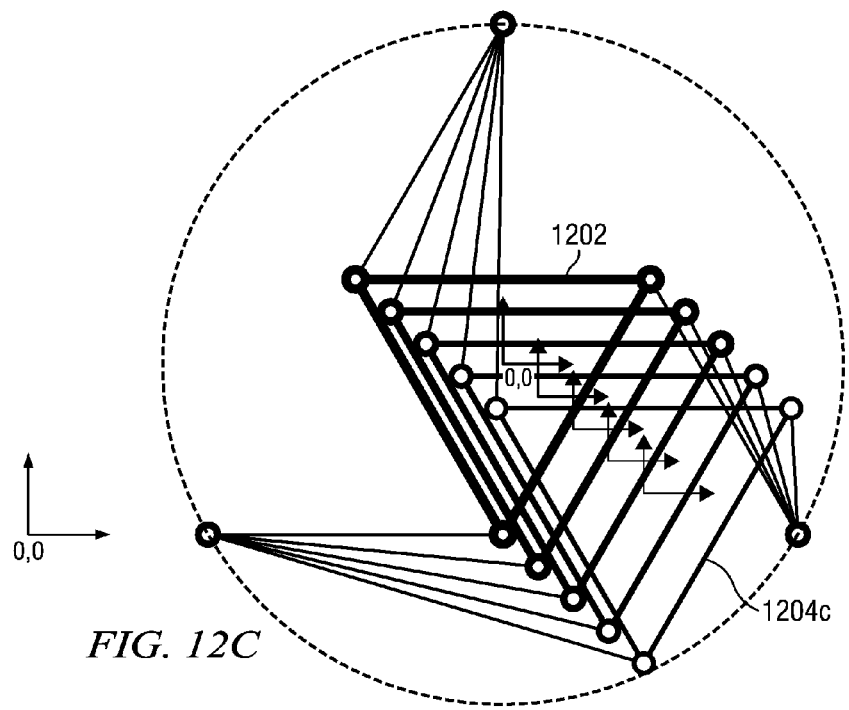
Figure 12D:
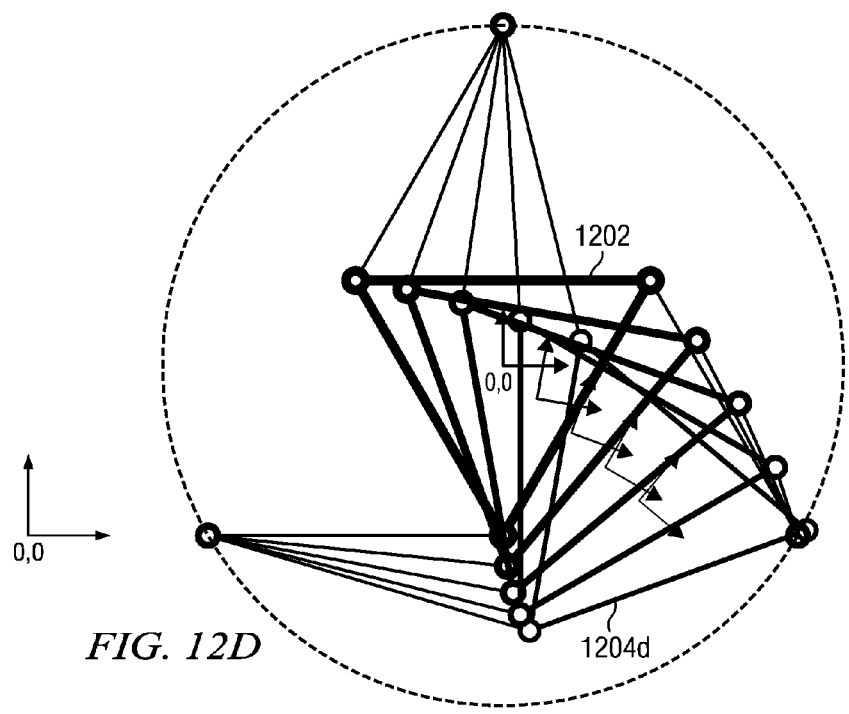
Figure 12E:
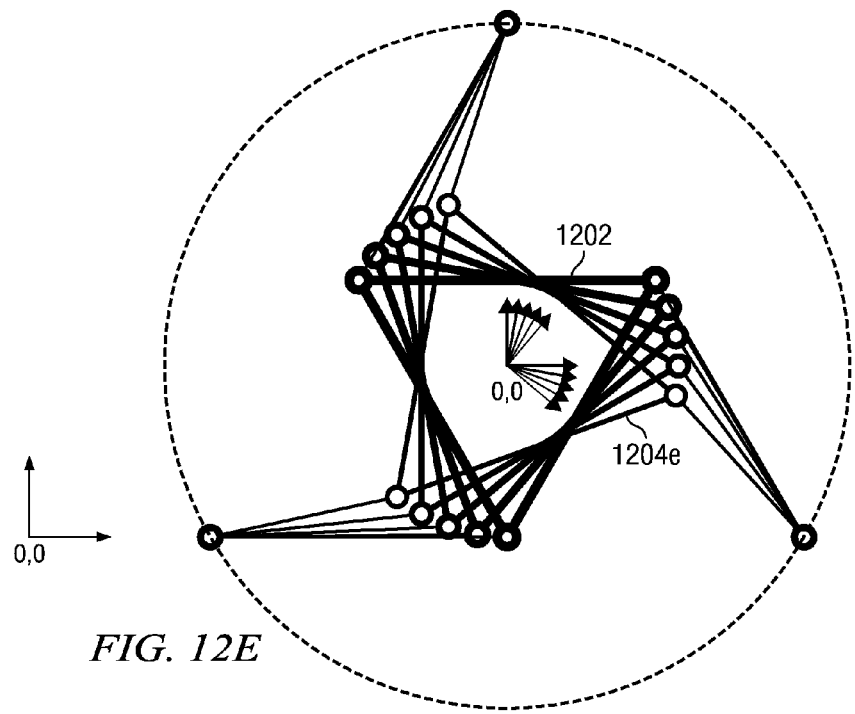
Figure 12F:
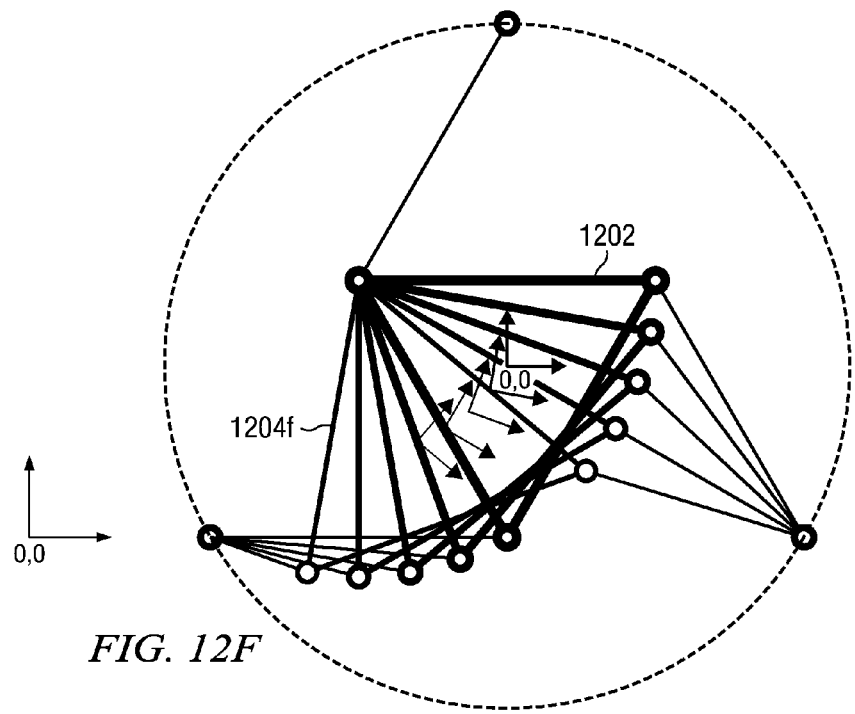
Figure 12G:
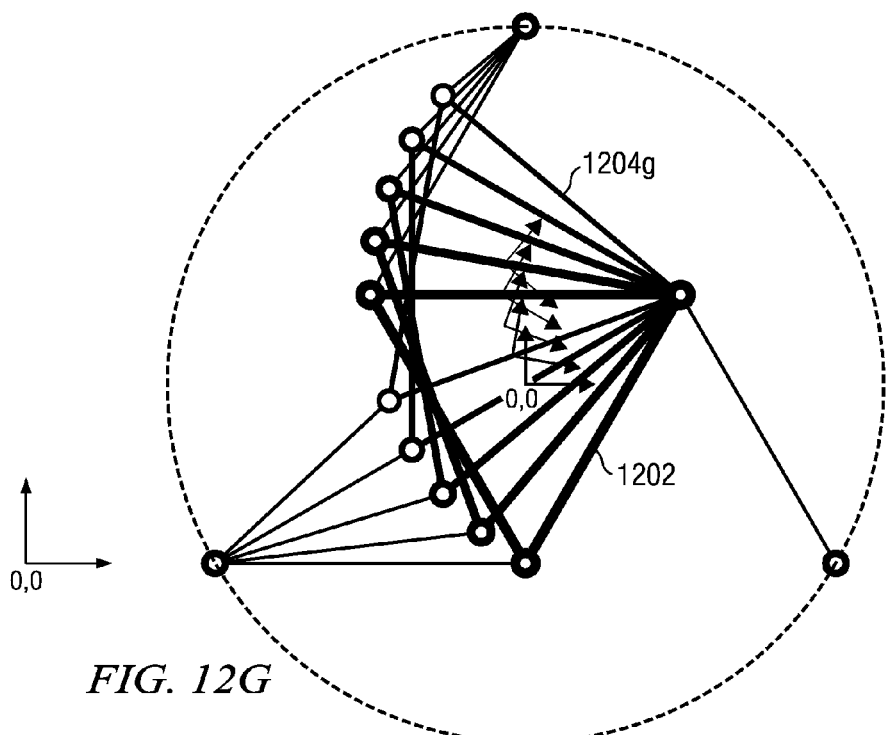
Figure 12H:
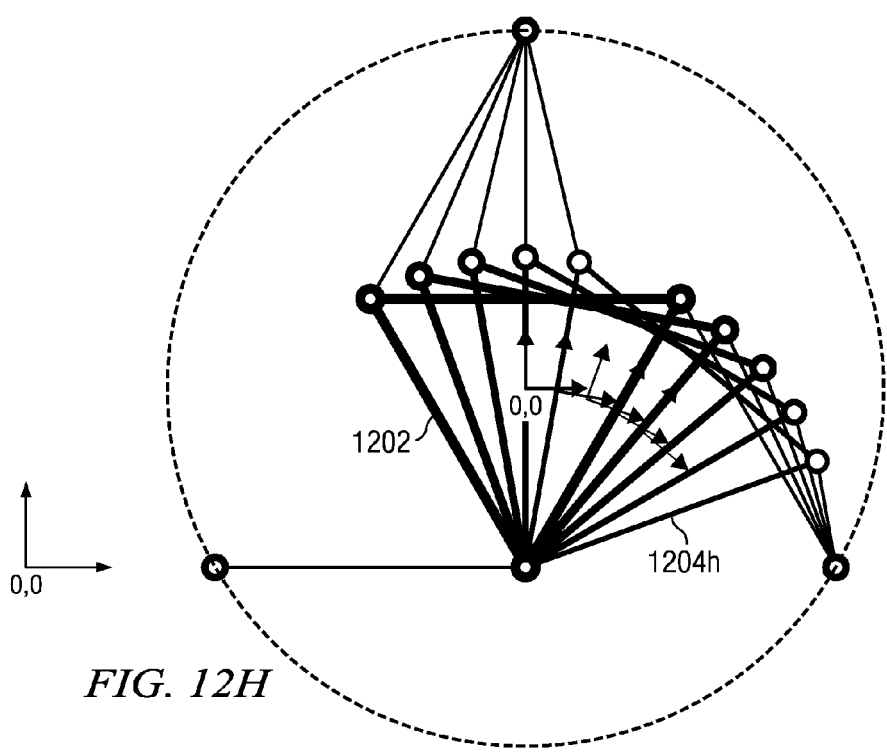

FIGS. 12A-H illustrate some of the possible motions of the test machine's actuator stage, e.g. lower mount 104 of FIG. 1A, according to an embodiment of the present invention. In each figure, the motions are illustrated by a sequence of poses of the stage that include an initial pose 1202, a final pose 1204a, 1204b, 1204c, 1204d, 1204e, 1204f, 1204g, 1204h, respectively, and three intermediate poses. FIGS. 12A and 12B illustrate x and y translations, respectively, while FIG. 12C illustrates combined x-y translation. FIG. 12D illustrates combined x-y translation coupled with a rotation about the center of the stage. Here, the stage moves in the X, Y direction and rotates about a center of rotation that itself moves along the X and Y axes. FIG. 12E illustrates pure rotation about the center of the stage (0,0), the center of the stage being an instant center of rotation, while FIGS. 12 F-H illustrate respective rotations about each of the vertices of the stage. In FIG. 12F, the upper left vertex of the stage (pose 1202) is an instant center of rotation. In FIG. 12G, the upper right vertex is an instant center of rotation, while in FIG. 12H, it is the lower vertex. Note that the center of rotation is freely programmable and is not limited to the several examples given in the figures.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims. For example, the actuators need not be hydraulic or linear and need not drive the sleeve of a Z actuator. The actuators could be pneumatic, electric, or powered by any other means.

What is claimed is:

1. A joint motion simulator to simulate biomechanical motion comprising:
   a mount to which a prosthetic device is mounted;
   actuators coupled to the mount to drive the mount; and
   a programmable controller to drive the actuators to translate the mount and to rotate the mount with a center of rotation controllable independent of translation, the center of rotation being an instant center of rotation.

2. A joint motion simulator as claimed in claim 1 wherein the actuators comprise at least three linear actuators.

3. A joint motion simulator as claimed in claim 2 further comprising a linear actuator to translate the mount in a linear direction substantially parallel to the axis of rotation.

4. A joint motion simulator as claimed in claim 3 wherein the linear actuator to translate comprises a piston within a sleeve, the piston being coupled to the mount and being hydraulically driven to translate the mount, and the at least three linear actuators are coupled to the sleeve.

5. A joint motion simulator as claimed in claim 4 wherein the at least three linear actuators are displaced vertically along the sleeve.

6. A joint motion simulator as claimed in claim 1 wherein the controller is programmed to vary the center of rotation with linear translation and rotation of the mount.

7. A joint motion simulator as claimed in claim 1 further comprising displacement sensors that measure displacement of the actuators.

8. A joint motion simulator as claimed in claim 7 wherein the controller drives the actuators based on the measured displacement.

9. A joint motion simulator to simulate a biomechanical motion comprising:
   a mount to which a prosthetic device is mounted;
   at least three linear actuators coupled to the mount to rotate the mount about an axis and translate the mount; and
   a linear actuator, distinct from the at least three linear actuators, to translate the mount in a linear direction substantially parallel to the axis of rotation.

10. A joint motion simulator as claimed in claim 9 wherein the linear actuator to translate the mount comprises a piston within a sleeve.

11. A joint motion simulator as claimed in claim 10 wherein the piston is coupled to the mount and being hydraulically driven to translate the mount, and the at least three linear actuators are coupled to the sleeve.

12. A joint motion simulator as claimed in claim 11 wherein the linear actuator to translate comprises a second piston coupled to the mount, the first and second pistons being driven in opposite directions.

13. A joint motion simulator as claimed in claim 11 wherein each of the at least three linear actuators comprises a piston hydraulically driven in a cylinder, the piston being coupled through a pin joint to the sleeve.

14. A joint motion simulator as claimed in claim 11 wherein the at least three linear actuators are displaced vertically along the sleeve.

15. A joint motion simulator as claimed in claim 9 further comprising a programmable controller to drive the actuators to translate the mount and to rotate the mount with a center of rotation controllable independent of translation.

16. A joint motion simulator as claimed in claim 15 further comprising a length sensor in each of the at least three linear actuators that measures length of the respective linear actuator.

17. A joint motion simulator as claimed in claim 16 wherein the controller drives the at least three linear actuators based on the measured lengths.

18. A joint motion simulator to simulate biomechanical motion comprising:
   a mount to which a prosthetic device is mounted;
   linear actuators coupled to the mount to drive the mount;
   length sensors that measure length of the linear actuators; and
   a programmable controller to drive the actuators based on the measured length to rotate the mount about an axis, to translate the mount in lateral directions relative to the axis of rotation and to laterally translate the axis of rotation independent of translation of the mount.

19. A joint motion simulator as claimed in claim 18 wherein the actuators comprise at least three linear actuators.

20. A joint motion simulator as claimed in claim 19 further comprising a linear actuator to translate the mount in a linear direction substantially parallel to the axis of rotation.

21. A joint motion simulator as claimed in claim 20 wherein the linear actuator to translate comprises a piston within a sleeve, the piston being coupled to the mount and being hydraulically driven to translate the mount, and the at least three linear actuators are coupled to the sleeve.

22. A joint motion simulator as claimed in claim 21 wherein the at least three linear actuators are displaced vertically along the sleeve.

23. A method of driving a prosthetic device to simulate joint motion comprising:
   driving the prosthetic device in rotation about an axis of rotation, the prosthetic device being mounted to a mount and being driven in rotation about the axis by driving linear actuators coupled to the mount to rotate the mount;
   moving the axis of rotation laterally in multiple directions by driving the linear actuators; and
   sensing length of the linear actuators.

24. A method of driving a prosthetic device as claimed in claim 23 wherein the actuators comprise at least three linear actuators.

25. A method of driving a prosthetic device as claimed in claim 23 further comprising driving the actuators to translate the mount in lateral directions relative to the axis of rotation.

26. A method of driving a prosthetic device as claimed in claim 25 wherein the axis of rotation is moved laterally independent of translation of the mount.

27. A method of driving a prosthetic device as claimed in claim 23 wherein driving the actuators includes driving the actuators based on the sensed length.

28. A method of driving a prosthetic device as claimed in claim 23 further comprising driving the prosthetic device in translation in a linear direction substantially parallel to the axis of rotation.

29. A joint motion simulator to simulate biomechanical motion comprising:
- a mount to which a prosthetic device is mounted;
- at least three linear actuators coupled to the mount to drive the mount;
- a linear actuator to translate the mount in a linear direction substantially parallel to the axis of rotation, the linear actuator to translate comprising a piston within a sleeve, the piston being coupled to the mount and being hydraulically driven to translate the mount, and the at least three linear actuators being coupled to the sleeve; and
- a programmable controller to drive the linear actuators to translate the mount and to rotate the mount with a center of rotation controllable independent of translation.

30. A joint motion simulator as claimed in claim 29 wherein the at least three linear actuators are displaced vertically along the sleeve.

31. A joint motion simulator as claimed in claim 29 wherein the controller is programmed to vary the center of rotation with linear translation and rotation of the mount.

32. A joint motion simulator as claimed in claim 29 further comprising displacement sensors that measure displacement of the actuators.

33. A joint motion simulator as claimed in claim 32 wherein the controller drives the actuators based on the measured displacement.

34. A joint motion simulator as claimed in claim 29 wherein the center of rotation is an instant center of rotation.

35. A joint motion simulator to simulate a biomechanical motion comprising:
- a mount to which a prosthetic device is mounted;
- at least three linear actuators coupled to the mount to rotate and translate the mount;
- a length sensor in each of the at least three linear actuators that measures length of the respective linear actuator; and
- a programmable controller to drive the actuators to translate the mount and to rotate the mount with a center of rotation controllable independent of translation.

36. A joint motion simulator as claimed in claim 35 wherein the controller drives the at least three linear actuators based on the measured lengths.

37. A joint motion simulator to simulate biomechanical motion comprising:
- a mount to which a prosthetic device is mounted;
- at least three linear actuators coupled to the mount to drive the mount;
- a linear actuator to translate the mount in a linear direction substantially parallel to the axis of rotation, the linear actuator to translate comprising a piston within a sleeve, the piston being coupled to the mount and being hydraulically driven to translate the mount, and the at least three linear actuators being coupled to the sleeve; and
- a programmable controller to drive the actuators to rotate the mount about an axis, to translate the mount in lateral directions relative to the axis of rotation and to laterally translate the axis of rotation independent of translation of the mount.

38. A joint motion simulator as claimed in claim 37 wherein the at least three linear actuators are displaced vertically along the sleeve.

* * * * *